(12) United States Patent
Washburn et al.

(10) Patent No.: US 8,529,897 B2
(45) Date of Patent: Sep. 10, 2013

(54) INFLAMMATION-REGULATING COMPOSITIONS AND METHODS

(75) Inventors: Newell Washburn, Pittsburgh, PA (US); Sidi Ahmed Bencherif, Boston, MA (US); Liang Tso Sun, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 125 days.

(21) Appl. No.: 12/673,583

(22) PCT Filed: Aug. 15, 2008

(86) PCT No.: PCT/US2008/073335
§ 371 (c)(1),
(2), (4) Date: Jan. 28, 2011

(87) PCT Pub. No.: WO2009/026158
PCT Pub. Date: Feb. 26, 2009

(65) Prior Publication Data
US 2011/0111035 A1    May 12, 2011

Related U.S. Application Data

(60) Provisional application No. 60/964,933, filed on Aug. 16, 2007.

(51) Int. Cl.
*A61K 39/00* (2006.01)
*A61K 39/395* (2006.01)
*A61K 38/00* (2006.01)

(52) U.S. Cl.
USPC ............... 424/134.1; 424/130.1; 424/145.1; 514/18.6

(58) Field of Classification Search
None
See application file for complete search history.

(56) References Cited

U.S. PATENT DOCUMENTS

| | | | |
|---|---|---|---|
| 5,120,829 A | 6/1992 | Pierschbacher et al. | |
| 5,654,267 A | 8/1997 | Vuori et al. | |
| 5,830,504 A | 11/1998 | Vuori et al. | |
| 6,284,503 B1 * | 9/2001 | Caldwell et al. | 435/181 |
| 6,870,033 B1 | 3/2005 | Hsei et al. | |
| 2004/0086508 A1 * | 5/2004 | Skurkovich et al. | 424/145.1 |

FOREIGN PATENT DOCUMENTS

| | | |
|---|---|---|
| DE | 102005046258 A1 | 3/2007 |
| WO | WO 90/06767 A1 | 6/1990 |

OTHER PUBLICATIONS

Barrientos et al. 2008. Wounds Rep and Reg. 16:585-601.*
Vazquez et al. 2003. Diabetes Res and Clin Practice 59:123-147.*
Yun et al. 2004. Biomaterials 25:147-157.*
Shah et al. 1992. Lancet. 339:213-214.*
Shu et al., Attachment and Spreading of Fibroblasts on an RGD Peptide-Modified Injectable Hyaluronan Hydrogel, *Journal of Biomedical Materials Research, Part A*, (Feb. 2004), 68(2):365-375.
Kaushik et al., CDP-870 (certolizumab) in Rheumatoid Arthritis, *Expert Opinion on Biological Therapy*, (Apr. 2005), 5(4):601-606.
Gonzalez et al., Transendothelial Migration Enhances Integrin-Dependent Human Neutrophil Chemokinesis, *Journal of Leukocyte Biology*, (Mar. 2007), 81(3):686-695.
Sun et al., Development of Cytokine-Regulating Matrices, *Wound Repair and Regeneration*, (Mar. 2008), 16(2):A16.
Boulton, The Diabetic Foot: A Global View, *Diabetes Metabolism Research and Reviews*, (Sep.-Oct. 2000), 16(1):S2-5.
Kantor et al., Treatment Options for Diabetic Neuropathic Foot Ulcers: A Cost-Effectiveness Analysis, *Dermatologic Surgery*, (Apr. 2001), 27(4):347-351.
Ramsey et al., Incidence, Outcomes, and Cost of Foot Ulcers in Patients with Diabetes, *Diabetes Care*, (Mar. 1999), 22(3):382-387.
Trengove et al., Mitogenic Activity and Cytokine Levels in Non-Healing and Healing Chronic Leg Ulcers, *Wound Repair and Regeneration*, (Jan.-Feb. 2000), 8(1):13-25.
Tarnuzzer et al., Biochemical Analysis of Acute and Chronic Wound Environments, *Wound Repair and Regeneration*, (Jul. 1996), 4(3):321-325.
Loppnow et al., Platelet-Derived Interleukin-1 Induces Cytokine Production, but not Proliferation of Human Vascular Smooth Muscle Cells, *Blood*, (Jan. 1998), 91(1):134-141.
Ishida et al., Absence of IL-1 Receptor Antagonist Impaired Wound Healing Along with Aberrant NF-κB Activation and a Reciprocal Suppression of TGF-β Signal Pathway, *Journal of Immunology*, (May 2006), 176(9):5598-5606.
Gallucci et al., Impaired Cutaneous Wound Healing in Interleukin-6-Deficient and Immunosuppressed Mice, *The FASEB Journal*, (Dec. 2000), 14(15):2525-2531.

(Continued)

*Primary Examiner* — Shulamith H Shafer
(74) *Attorney, Agent, or Firm* — Pepper Hamilton LLP

(57) ABSTRACT

The various embodiments provide a composition that provides local control over inflammation. The composition localizes the activities of the cytokine-neutralizing antibodies to the site of inflammation through covalent attachment to hydrophilic matrices. The various embodiments including a hydrophilic polymer, a ligand binding moiety covalently attached to the polymer, and optionally, a cellular adhesion peptide covalently attached to the polymer. The hydrophilic polymer may be a glycosaminoglycan such as hyaluronan. The cellular adhesion peptide may be a linear RGD peptide sequence covalently attached to the polymer. The ligand binding moiety may be a monoclonal antibody covalently attached to the polymer. The antibody may be selected from the group consisting of an anti-IL-1β, an anti-IL-6, an anti-TNF-α, and combinations thereof. The polymer functions as a substrate or matrix for cell migration and tissue regeneration. The RGD peptide functions to promote cellular proliferation, migration and attachment to the polymer. The monoclonal antibody functions to inhibit the inflammatory response.

12 Claims, 10 Drawing Sheets

(56) References Cited

OTHER PUBLICATIONS

Mori et al., Accelerated Wound Healing in Tumor Necrosis Factor Receptor p55-Deficient Mice with Reduced Leukocyte Infiltration, *The FASEB Journal*, (Jul. 2002), 16(9):963-974.

Streit et al., Topical Application of the Tumour Necrosis Factor-α Antibody Infliximab Improves Healing of Chronic Wounds, *International Wound Journal*, (Sep. 2006), 3(3):171-179.

Nixon et al., The Efficacy of Inhibiting Tumour Necrosis Factor α and Interleukin 1 in Patients with Rheumatoid Arthritis: A Meta-analysis and Adjusted Indirect Comparisons, *Rheumatology (Oxford Journals)*, (Jul. 2007), 46(7):1140-1147.

Genovese et al., Combination Therapy with Etanercept and Anakinra in the Treatment of Patients with Rheumatoid Arthritis Who Have Been Treated Unsuccessfully with Methotrexate, *Arthritis and Rheumatism*, (May 2004), 50(5):1412-1419.

Steed et al., Promotion and Acceleration of Diabetic Ulcer Healing by Arginine-Glycine-Aspartic Acid (RGD) Peptide Matrix, *Diabetes Care*, (Jan. 1995), 18(1):39-46.

Savani et al., Differential Involvement of the Hyaluronan (HA) Receptors CD44 and Receptor for HA-Mediated Motility in Endothelial Cell Function and Angiogenesis, *Journal of Biological Chemistry*, (Sep. 2001), 276(39):36770-36778.

Steed, Clinical Evaluation of Recombinant Human Platelet-Derived Growth Factor for the Treatment of Lower Extremity Diabetic Ulcers, *Journal of Vascular Surgery*, (Jan. 1995), 21(1):71-78.

Wethers et al., Accelerated Healing of Chronic Sickle-Cell Leg Ulcers Treated with RGD Peptide Matrix. RGD Study Group, *Blood*, (Sep. 1994), 84(6):1775-1779.

Ruoslahti et al., Arg-Gly-Asp: A Versatile Cell Recognition Signal, *Cell*, (Feb. 28, 1986), 44(4):517-518.

Ruoslahti et al., New Perspectives in Cell Adhesion: RGD and Integrins, *Science*, (Oct. 1987), 238(4826):491-497.

Ruoslahti et al., Integrins, *J. Clin. Invest*, (Jan. 1991), 87(1):1-5.

* cited by examiner

Macrophage phenotype determined by pro- and anti-inflammatory signals

A                           B

Saline-treated control

HA-RGD control

HA-RGD-anti-TNF-α

INFLAMMATION-REGULATING COMPOSITIONS AND METHODS

RELATED APPLICATIONS

This application is a National Stage entry of International Application No. PCT/US2008/073335 filed on 15 Aug. 2008, which is incorporated herein by reference in its entirety, which claims priority from U.S. Provisional Patent Application Ser. No. 60/964,933 filed 16 Aug. 2007, which is incorporated herein by reference.

FEDERAL RESEARCH STATEMENT

This invention was made in part with United States Government support under the United States Department of Defense, Department of the Army, Military Medical Research and Development grant DAMD17-02-1-0717. Therefore, the United States Government may have certain rights in the invention.

FIELD OF THE INVENTION

Compositions and methods for treating chronic degenerative inflammatory conditions by enhancing cell growth and tissue regeneration while simultaneously inhibiting the inflammatory response are disclosed.

Biological tissue is comprised of cells and extracellular matrix. The structure and strength of tissue is a consequence of the interaction between the cells and the extracellular matrix. The extracellular matrix is comprised of proteins and glycoproteins such as collagen, elastin, fibronectin, vitronectin and laminin; polysaccharides such as the glycosaminoglycan ("GAG") hyaluronic acid; and proteoglycans such as aggrecan, decorin and perlecan. Cells attach directly to each other and to the extracellular matrix, which supports the attachment of cells, serves as a scaffold or structural support for cells, mechanically regulates cellular functions via cell adhesion, lubricates cells and provides a transport system for intercellular mediators, nutrients and waste products.

Acute wounds normally heal in an orderly and efficient manner by progressing through four distinct but overlapping phases: hemostasis, inflammation, proliferation and remodeling. Throughout these phases, cells and the extracellular matrix ("ECM") play an important role in regulating and integrating many key processes of healing.

The hemostasis phase of wound healing involves the formation of a provisional wound matrix. The clot that forms at the site of an injury not only stops bleeding, but deposits a host of plasma and cell-secreted constituents at the wound interface. Epidermal cells subsequently dissect their way under the clot and over the granulation tissue (which is comprised of a dense population of macrophages, fibroblasts and newly formed blood vessels embedded in a loose matrix of fibrin, fibronectin, collagen and other ECM proteins). Stimulation of the clotting cascade results in the proteolytic cleavage of fibrinogen by the enzyme thrombin, forming an insoluble fibrin clot that holds damaged tissues together and provides the provisional matrix. In addition, the clot contains fibronectin molecules that are present in plasma and bind to fibrin through fibrin-specific binding sites.

The inflammatory response involves the migration of neutrophils, macrophages and lymphocytes to the site of the injury. Neutrophils are the first inflammatory cells to respond to the soluble mediators released by platelets and the coagulation cascade. Their primary role is to mount the first line of defense against infection by phagocytosing and killing bacteria, and by breaking down foreign materials and devitalized tissue. Neutrophils also produce and release inflammatory mediators such as tumor necrosis factor alpha ("TNF-$\alpha$") and interleukin-1 ("IL-1"), which further recruit and activate neutrophils and macrophages. In this way early inflammatory signals can induce massive responses at the site of injury through positive signaling loops that involve these soluble signaling proteins. Neutrophils also produce and contain high levels of proteases and oxygen free radicals, which they use to break down the surrounding tissue. In healthy patients, this process is necessary to establish the proper environment for the later stages of tissue repair. Neutrophils release these substances into the local wound area upon cell death, which can cause extensive tissue damage and prolong the inflammatory phase. The persistent presence of high levels of bacteria in a wound may contribute to chronicity through continued recruitment of neutrophils and their release of proteases, cytokines and intracellular contents.

Neutrophils are usually depleted in an acute wound after two to three days and are replaced by tissue macrophages. Tissue macrophages function as phagocytes that ingest bacteria, devitalized tissue and depleted neutrophils, and produce collagenases and elastase to enzymatically mediate the degeneration of devitalized tissues. They are able to regulate proteolytic destruction of tissue in the wound by producing and secreting inhibitors for these enzymes.

Fibroblasts migrate into the provisional wound matrix as part of angiogenesis and in response to chemotactic growth factors released by platelets from the wound area and subcutaneous tissue and begin to express new integrin receptors. The integrin receptors then generate new intracellular signals that stop the fibroblasts from migrating. Growth factors and proteins contained within the provisional wound matrix help to stimulate fibroblasts to begin proliferating and synthesizing new collagen and other ECM components. In this way the provisional wound matrix functions as a reservoir to help trap growth factors and actively signals fibroblasts, epidermal cells and vascular endothelial cells, via their integrin receptors, to transform into activated wound cells that will repair the injury.

Macrophages also mediate the transition from the inflammatory phase to the proliferative phase of normal healing. They release a wide variety of growth factors and cytokines, including TNF-$\alpha$, transforming growth factor beta ("TGF-$\beta$"), platelet-derived growth factors ("PDGFs"), IL-1, interleukin six ("IL-6"), insulin-like growth factor-one ("IGF-1") and fibroblast growth factor ("FGF"). Some of these soluble mediators recruit and activate fibroblasts, which will synthesize, deposit and organize the new tissue matrix, while others promote angiogenesis. FIG. 1 illustrates the M1 and M2 macrophage phenotypes. The M1 phenotype produces pro-inflammatory mediators. The M2 phenotype produces pro-angiogenic factors and mediators of tissue repair and remodeling.

During the proliferative phase, the provisional wound matrix is remodeled and replaced with scar tissue, consisting of new collagen fibers, proteoglycans and elastin fibers, which partially restore the structure and function of the tissue. This is accomplished by the migration, proliferation and differentiation of epithelial cells, fibroblasts and vascular endothelial cells from adjacent uninjured tissue and stem cells that originate in the bone marrow and circulate to the wound site.

Fibroblasts migrate into the wound in response to soluble cytokines and growth factors, which are initially released from platelets when they degranulate and later by macrophages in the wound. These include PDGF, TGF-$\beta$ and FGF. Fibroblasts secrete proteases called matrix metalloproteinases ("MMPs") which are essential for the migration of cells through the ECM. For example, collagenase ("MMP-1") cuts intact collagen at a single site, gelatinases ("MMP-2" and "MMP-9") degrade partially denatured collagen (gelatin), and stromelysin ("MMP-3") degrades multiple protein substrates in the ECM. In addition, MMPs remove collagen and other ECM components that were denatured during the injury. Partially degraded collagen molecules will not bind properly with new collagen molecules synthesized during scar formation, resulting in disorganized, weak ECM, so the degraded collagen molecules must be removed by controlled action of the MMPs. However, this process must be carefully controlled by tissue inhibitors of metalloproteinases (TIMPs) enzymes, which prevent the MMPs from degrading intact, functional matrix.

After the fibroblasts have migrated into the provisional wound matrix, they proliferate and begin to synthesize new collagen, elastin, proteoglycans and other components that comprise granulation tissue. PDGF and TGF-β are two of the important growth factors that regulate the expression of ECM genes and proteases in fibroblasts. Cells from surrounding tissues begin to proliferate and migrate into the wound site, bind to the newly deposited matrix and form scar tissue.

Remodeling is the final phase of wound healing and occurs through the actions of several different classes of proteolytic enzymes such as MMPs and serine proteases produced by cells in the wound bed at different times during the healing process. Specific MMP proteases that are necessary for wound healing are the collagenases, which degrade intact fibrillar collagen molecules; the gelatinases, which degrade damaged fibrillar collagen molecules; and the stromelysins, which degrade proteoglycans. Under normal conditions, the destructive actions of proteolytic enzymes are carefully regulated by TIMP enzymes, which are produced by cells in the wound bed.

A chronic wound is a wound that does not heal in a normal manner and in a predictable amount of time. Several common medical conditions are associated with chronic wounds, including diabetic ulcers, decubitus/pressure ulcers, venous ulcers, severe burns, ischemia and anemia, for example. Statistics on patients diagnosed with diabetes, for example, indicate that more than 14.6 million diabetics are at an increased risk of foot ulceration at a rate of 15% at some point in their lifetime. See Boulton A. J., "The diabetic foot: a global view," Diabetes Metab. Res. Rev., 16 Suppl 1:S2-5. September-October 2000; and Kantor J. et al., "Treatment options for diabetic neuropathic foot ulcers: a cost-effectiveness analysis," Dermatol. Surg., 27(4):347-351 (April 2001). This complication represents a significant fraction of the cost of caring for patients with diabetes, estimated to range from 25% to 50%, and diabetic foot ulcers are the most important risk factor for lower extremity amputation at a rate of approximately 15.6%. See Ramsey S. D. et al., "Incidence, outcomes, and cost of foot ulcers in patients with diabetes," Diabetes Care 22(3):382-387 (March 1999).

Chronic wounds generally involve uncharacteristically slow healing, abnormal healing, or a complete lack of healing. Acute normal-healing wounds are characterized by a precise balance between degradation and regeneration of damaged tissue throughout the four phases of healing described above. Chronic wounds, however, are characterized by a retarded healing trajectory where the proliferative phase fails to initiate and a prolonged or indefinite inflammatory phase occurs. In the sustained inflammatory phase, degradation predominates and regeneration of the damaged tissue is minimal to non-existent. This lengthened inflammatory phase may cause increased levels of proteases such as MMPs, elastase, plasmin and thrombin. The increased levels of protein can destroy components of the ECM and damage the growth factors and their receptors that are essential for transitioning from the inflammatory phase to the proliferative phase of the healing response. Accordingly, chronic wounds are often characterized by incomplete closure and increased incidence of infection.

The pathophysiology of chronic wounds varies according to the underlying medical condition. However, all chronic wounds are characterized by several common features including increased levels of pro-inflammatory mediators relative to acute or properly healing wounds. Pro-inflammatory mediators are substances secreted by cells as part of a host response to disease or infection that promote inflammation. Pro-inflammatory mediators include prostaglandins, histamines, bradykinin, complement proteins, chemokines and cytokines such as IL-1, IL-6, IL-8, IL-12, IL-18, nitric oxide ("NO"), monocyte chemoattractant protein-1 ("MCP-1"), and interferon gamma ("IFN-γ"), for example.

Increased levels of the cytokines IL-1β, IL-6 and TNF-α have been measured in chronic wounds relative to acute wounds. For example, in wound fluid from healing versus non-healing leg ulcers, the median concentration of IL-1β was found to be 7785 pg/ml versus 17,902 pg/ml, the median concentration of IL-6 was found to be 55,185 pg/ml versus 77,762 pg/ml, and the median concentration of TNF-α was found to be 1639 pg/ml versus 4734 pg/ml. See Trengove et al., "Mitogenic activity and cytokine levels in non-healing and healing chronic leg ulcers," Wound Repair Regen, 8, 13-25 (2000). In a comparison of chronic wounds and acute wounds from mastectomies, 100-fold increases in IL-1β and TNF-α and a six-fold increase in IL-6 were measured. See Tarnuzzer et al., "Biochemical analysis of acute and chronic wound environments," Wound Repair Regen., 4, 321-325 (1996).

In acute wounds, IL-1β activates neutrophils, promotes chemotaxis, and stimulates cytokine production in the surrounding tissue. It has been demonstrated that by increasing the activity of IL-1β in knock-out (KO) mice lacking the IL-1β receptor antagonist (IL-1ra) increases neutrophil invasion at the wound site and significantly lengthens the time for wound closure. (See Loppnow et al., "Platelet-derived interleukin-1 induces cytokine production, but not proliferation of human vascular smooth muscle cells," Blood, 91, 134-141 (1998); and Ishida et al., "Absence of IL-1 receptor antagonist impaired wound healing along with aberrant NF-kappa-B activation and a reciprocal suppression of TGF-beta signal pathway," J Immunol, 176, 5598-5606 (2006)). Comparisons of histology data in wild type (WT) and IL-1ra knock-out (KO) mice demonstrated that neutrophil recruitment in KO mice two days after wounding was nearly double that in WT mice. The data following wound closure over 14 days showed a significant inhibition of closure in the KO mice.

It has been demonstrated that wounds in IL-6 KO mice took up to three times longer to heal than those of WT controls. See Gallucci et al., "Impaired cutaneous wound healing in interleukin-6-deficient and immunosuppressed mice." FASEB J, vol. 14, pp. 2525-2531 (2000). Wounds in these animals were characterized by a significant delay in re-epithelialization and inhibition of the formation of granulation tissue. A comparison of the area of the healing wound in WT versus IL-6 KO mice quantified over 15 days show that IL-6 KO mice had a five-day delay in the onset of healing.

It has also been reported that KO mice lacking the TNF-α receptor p55 showed accelerated wound healing, characterized by increases in re-epithelialization, collagen production, angiogenesis, and expression of TGF-β1, vascular endothelial growth factor, and connective tissue growth factor. See Mori et al., "Accelerated wound healing in tumor necrosis factor receptor p55-deficient mice with reduced leukocyte infiltration," FASEB J, 16, 963-974 (2002). Comparisons of wound closure in WT and TNF-α KO mice show that wound closure over a 14 day period was enhanced in the TNF-α KO mice. In WT mice, there was significant invasion of neutrophils up to 6 days, but in the KO mice, both neutrophil and macrophage invasion was significantly inhibited.

Strategies for treating chronic wounds include debridement, in which surface debris and necrotic tissue is removed and topical application of growth factors, such as PDGF, FGF-2, and TGF-β. However, the underlying tissue often does not heal better than the debrided tissue, and topical application of free growth factors does not appear to be a substantially effective therapy.

Inhibiting pro-inflammatory cytokines has been shown to be an effective strategy for promoting healing of chronic wounds. Infliximab, a human monoclonal antibody that binds TNF-α and inhibits its signaling, was shown to promote wound closure in patients suffering from chronic ulcers, with 5 of 14 ulcers showing complete closure after 8 weeks. See Streit M. et al., "Topical application of the tumour necrosis factor-alpha antibody infliximab improves healing of chronic wounds, "Int. Wound J., 3(3):171-179 (September 2006) An antagonist against the IL-1β receptor, anakinra, has also been developed to treat inflammatory conditions, such as rheumatoid arthritis. Although the clinical trails showed some efficacy, anakinra has been found to be less effective in treating these conditions than therapeutics that target TNF-α. See Nixon R. et al., "The efficacy of inhibiting tumour necrosis factor {alpha} and interleukin 1 in patients with rheumatoid arthritis: a meta-analysis and adjusted indirect comparisons, "Rheumatology (Oxford), 46(7):1140-1147 (July 2007). An important caveat is the contraindication against taking therapeutics that inhibit signaling from both TNF-α and IL-1β. When patients suffering from rheumatoid arthritis were given both etanercept and anakinra, there was a statistically insignificant (P=0.914) improvement in outcome compared to etanercept alone, but a significant increase in the risk of infection (0% for etanercept alone; 3.7-7.4% for the combination therapy) was observed. See Genovese M. C. et al., "Combination therapy with etanercept and anakinra in the treatment of patients with rheumatoid arthritis who have been treated unsuccessfully with methotrexate," Arthritis Rheum., 50(5):1412-1419 (May 2004)

Additional strategies for healing chronic wounds include using a viscous matrix consisting of hyaluronic acid covalently modified with the arginine-glycine-aspartic acid ("RGD") peptide. See Steel et al., Diabetes Care, 18: 39-46 (1995). Further strategies involve compositions consisting of biodegradable polymer, RGD peptide, and a ligand such as a ligand to a PDGF receptor, a ligand to an insulin receptor, a ligand to an interleukin four ("IL-4") receptor, and a ligand to an IGF receptor. See U.S. Pat. Nos. 5,654,267 and 5,830,504, incorporated by reference herein.

Hyaluronic acid is a hydrophilic material that is recognized by the CD44 receptor and receptor for HA-mediated motility (RHAMM) in multiple cell types and promotes a motile phenotype. See Savani R. C. et al., "Differential involvement of the hyaluronan (HA) receptors CD44 and receptor for HA-mediated motility in endothelial cell function and angiogenesis," J. Biol. Chem., 276(39):36770-36778 (Sep. 28, 2001) Furthermore, HA degradation products are known damage-associated molecular patterns that may recruit additional repair cells to the wound site. In clinical trials on diabetic foot ulcers, the HA-RGD matrix promoted complete healing in 35% (14 of 40) patients as compared to 8% (2 of 25) in the control group that received a saline solution placebo. See Steed D. L., "Clinical evaluation of recombinant human platelet-derived growth factor for the treatment of lower extremity ulcers," Plast. Reconstr. Surg. 117 (7 Suppl):143S-149S (June 2006). Similar results were observed when RGD-HA was used to treat leg ulcers in patients with sickle-cell anemia. See Wethers D. L. et al., "Accelerated healing of chronic sickle-cell leg ulcers treated with RGD peptide matrix. RGD Study Group," Blood 84(6):1775-1779 (Sep. 15, 1994). While these various therapies show improvements in patient outcomes, there remains a critical, unmet need for effective, and cost-effective, therapies to heal chronic wounds.

BRIEF SUMMARY

None of the approaches to treating chronic wounds addresses both the prolonged inflammatory phase and the failure to initiate the proliferative phase of healing. Therefore, there remains a need for an effective agent to simultaneously mediate the prolonged inflammatory response and promote cell proliferation, migration and attachment to initiate the proliferative phase of wound healing in chronic wounds.

Chronic wounds are further characterized by an increase in protease activities at the wound site, especially in the activities of MMPs. For example, collagenases (MMP-1) and gelatinases (MMP-2 and MMP-9) work together to substantially degrade constitutive structural proteins, leading to an extracellular matrix that is significantly eroded in the wound. Moreover, there may be a dysregulation in growth factor activity in chronic wounds locked into a continuous inflammatory phase and unable to proceed to the proliferative phase in which growth factors would be the central determinants of the healing trajectory.

Inflammatory mediators such as the cytokines play a central role in determining the balance of biochemical factors at the wound site. Pro-inflammatory mediators, such as the cytokines IL-1β, IL-6, and TNF-α, induce the expression of several collagenases, including MMP-1, MMP-2, and MMP-9, which promote the chronic non-healing wound state. Elevated MMP expression due to increased inflammatory mediator levels further perpetuates the chronic wound state by proteolytically inactivating important growth factors such as PDGF and vascular endothelial growth factor ("VEGF"). Furthermore, TNF-α and TGF-β synergistically promote the production of MMP-9 by fibroblasts. Pro-inflammatory mediators also inhibit collagen synthesis in cultured fibroblasts, effectively inhibiting the deposition of new tissue.

The production of cytokines and other pro-inflammatory mediators is often autoinductive, and exposure to a low concentration of mediators can lead to a signaling cascade and the production of more mediators. Chronic wounds appear to lack mechanisms capable of controlling mediator production, resulting in an imbalance in their concentrations. Therefore, restoring this balance is an effective approach for treating chronic wounds. When treated with a composition as described herein that inhibits the activity of pro-inflammatory mediators, such as IL-1β, IL-6, and TNF-α, or TGF-β activity, a concomitant reduction in neutrophil invasion is expected, coupled with an increase in rate of wound closure.

The various embodiments of the invention described herein provide a composition that provides local control over inflammation. For example, in various embodiments the composition localizes the activities of the cytokine-neutralizing antibodies to the site of inflammation through covalent attachment to hydrophilic matrices. In one general aspect, the various embodiments of the invention are directed to a composition including a hydrophilic polymer and a ligand binding moiety covalently attached to the polymer. Optionally, a cellular adhesion peptide may be covalently attached directly to the polymer or attached to the polymer through a linker. The various embodiments directed to the use of the various embodiments of the composition of the invention provides local control over the inflammatory process.

In various embodiments, the composition may be comprised of a novel gel based on antibodies against pro-inflammatory mediators, such as cytokines, that have been covalently incorporated in a gel-forming matrix. While not wishing to be bound by theory, it is believed that by covalently attaching neutralizing antibodies against pro-inflammatory mediators, for example, in a gel, in a colloidal suspension, or spread on a woven substrate, it will be possible to restrict their activities to the injury site, thus allowing aggressive targeting of the mediators of inflammation without risking systemic effects. The compositions of the present invention are designed to control mediators of inflammation to ensure the natural transition to healing ending in tissue regeneration.

In various embodiments, the composition may comprise a hyaluronan gel matrix and an antibody, preferably a monoclonal antibody, covalently attached to the hyaluronan matrix. The antibody may be selected from the group consisting of an anti-IL-1β, an anti-IL-6, an anti-TNF-α, and combinations thereof. The hyaluronan gel matrix may function to promote cellular migration and attachment. The antibody functions to inhibit the inflammatory response. The composition may also include a linear RGD peptide sequence covalently attached to the hyaluronan matrix.

The invention also includes various embodiments of a method of treatment comprising locally administering any of the inflammation regulating compositions described herein to a patient in need of such treatment. The composition may be used, for example, to treat chronic wounds or inflammation arising from condition selected from the group consisting of a pressure ulcer, a venous ulcer, and a diabetic ulcer. The composition may be used to treat a dermal wound. In another embodiment of the treatment method, the composition may be used to treat an inflammatory bowel disease. In another embodiment of the treatment method, the composition may be used to treat rheumatoid arthritis.

The method of treatment may include topically administering the composition directly in a wound. In another embodiment, the method of treatment may include locally administering the composition by hypodermic injection.

BRIEF DESCRIPTION OF THE DRAWINGS

The various embodiments may be understood by reference to the following description, taken with the accompanying drawings as follows.

DETAILED DESCRIPTION

Figure 1:
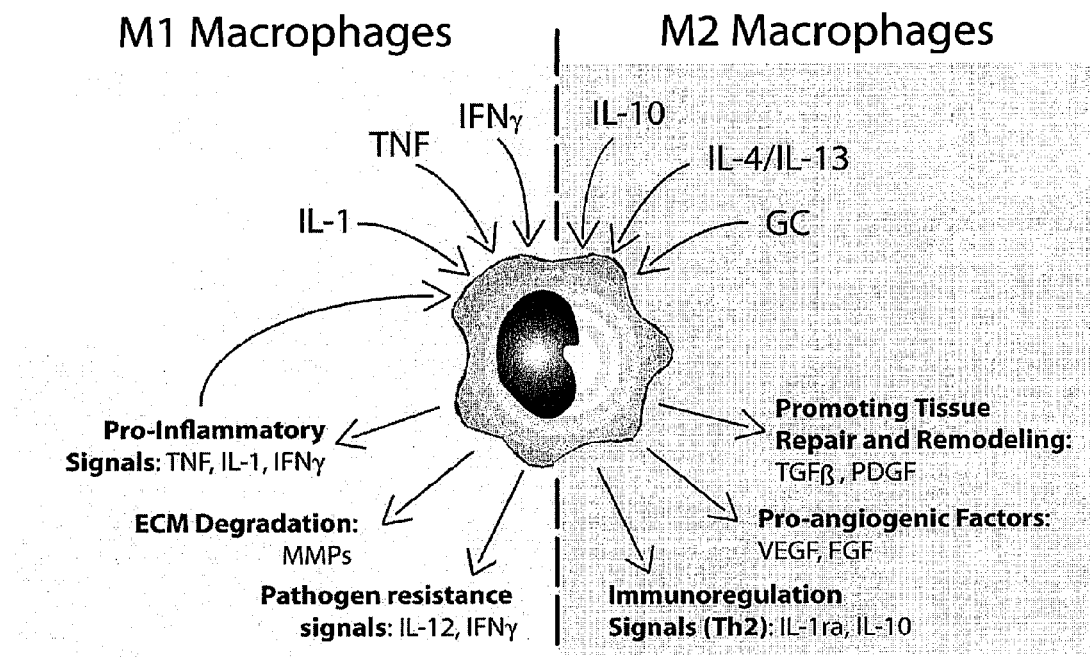
FIGS. 1A-B schematically illustrate the macrophage phenotypes M1 and M2 determined by pro- and anti-inflammatory signals.

It is to be understood that certain descriptions of the present invention have been simplified to illustrate only those elements and limitations that are relevant to a clear understanding of the present invention, while eliminating, for purposes of clarity, other elements. Those of ordinary skill in the art, upon considering the present description of the invention, will recognize that other elements and/or limitations may be desirable in order to implement the present invention. However, because such other elements and/or limitations may be readily ascertained by one of ordinary skill upon considering the present description of the invention, and are not necessary for a complete understanding of the present invention, a discussion of such elements and limitations is not provided herein. As such, it is to be understood that the description set forth herein is merely exemplary to the present invention and is not intended to limit the scope of the claims.

Other than in the examples herein, or unless otherwise expressly specified, all of the numerical ranges, amounts, values, and percentages, such as those for amounts of materials, elemental contents, times and temperatures of reaction, ratios of amounts, and others, in the following portion of the specification and attached claims may be read as if prefaced by the word "about," even though the term "about" may not expressly appear with the value, amount, or range. Accordingly, unless indicated to the contrary, the numerical parameters set forth in the following specification and claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains error necessarily resulting from the deviation found in its underlying respective testing measurements. Furthermore, when numerical ranges are set forth herein, these ranges are inclusive of the recited range end points (i.e., end points may be used). Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value equal to or less than 10.

All patents, publications, or other disclosure material referenced herein are incorporated by reference in their entirety. Any patent, publication, or other disclosure material, in whole or in part, that is incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The articles "a," "an," and "the" are used herein to refer to one or more than one (i.e., to at least one) of the grammatical objects of the article. By way of example, "a component" means one or more components, and thus, possibly, more than one component is contemplated and may be employed or used.

The various embodiments provide a composition that provides local control over inflammation. For example, in various embodiments the composition localizes the activities of the cytokine-neutralizing antibodies to the site of inflammation through covalent attachment to hydrophilic matrices. The various embodiments relate, in general, to inflammation regulating compositions for the local treatment of inflammatory conditions. The composition reduces inflammation at, for example, a wound site, and promotes, or at least reduces or removes the barriers to tissue regeneration. The compositions in various embodiments, generally includes a hydrophilic polymer and a ligand binding moiety attached to the polymer. A cellular adhesion peptide may optionally be attached to the polymer. The ligand binding moiety can bind and in some embodiments, neutralize inflammatory mediators.

The compositions and methods described herein can simultaneously address at least two problems with chronic wounds: the continuous inflammatory phase and the failure to proceed to the proliferative phase. The compositions described herein promote cell proliferation, migration and attachment in a wound that results in tissue regeneration, while simultaneously sequestering the increased levels of pro-inflammatory mediators present in a wound, thereby inhibiting the inflammatory response. Compositions useful in practicing these treatments include a hydrophilic polymer, a ligand binding moiety covalently attached to the polymer, and optionally, a cellular adhesion peptide covalently attached to the polymer.

In some embodiments, the hydrophilic polymer serves as a substrate that allows localized delivery of the ligand binding moiety to the wound site. The hydrophilic polymer further provides a scaffold or matrix for cellular ingrowth, and can be biodegradable/bioerodable. The hydrophilic polymer may be selected such that it promotes cell proliferation, cell migration and cell adhesion to the composition, which in turn promotes tissue regeneration and repair in the wound. The optional cellular adhesion peptide further promotes cell proliferation, cell migration and cell adhesion to the composition. The ligand binding moiety is capable of binding pro-inflammatory mediators locally present in the wound. The bound pro-inflammatory mediators are effectively removed from the wound and prevented from perpetuating the inflammatory response. The concurrent action of the hydrophilic polymer matrix, the ligand binding moiety, and the optional cellular adhesion peptide arrest the persistent inflammatory response and simultaneously induce the proliferative phase of normal wound healing.

In certain embodiments, the ligand binding moiety is capable of neutralizing a pro-inflammatory mediator. For example, an antibody to TNF-α can bind the receptor binding site, thereby acting as a competitive inhibitor. In other embodiments the neutralizing ligand binding moiety is capable of partially denaturing the ligand, thus making it unable to bind its physiological target, such as a cell surface receptor. Whether a neutralizing or non-neutralizing ligand binding moiety is used, will depend on the application. For example, a neutralizing ligand binding moiety is particularly useful where a cell can infiltrate and/or adhere to the functionalized polymer. In such embodiments, soluble pro-inflammatory mediators are effectively masked from binding the cognate ligands on the infiltrating cells. In the alternative, a non-neutralizing antibody may be particularly useful where the polymer matrix is not accessible to cellular effector cells, such as when the functionalized polymer is non-biodegradable. In such instances, the polymer matrix acts like a sponge that specifically depletes pro-inflammatory mediators from the wound site. Such functionalized polymers are particularly useful as replaceable wound dressings in contrast to implants that are placed within the wound site.

Without wishing to be bound by theory, it is believed that IL-6 may contribute to the initiation of the healing response, potentially via its mitogenic effects on wound-edge keratinocytes and via its chemoattractive effect on neutrophils Inhibition of IL-6 signaling therefore has an effect on healing. Further, inhibition of TNF-α signaling by the compositions described herein appears to both inhibit inflammatory responses and promote healing.

In certain other embodiments, a non-neutralizing ligand binding moiety is used. For example, if the ligand binding moiety is a non-neutralizing anti TGF-β antibody, the immune response can be further down-regulated, since TGF-β is anti-inflammatory. Thus, in some embodiments, the functionalized polymer may comprise a neutralizing antibody or receptor for, for example, IL-6 as well as a non-neutralizing antibody or receptor for TGF-β, thereby decreasing the IL-6 mediated inflammatory response, while increasing the anti-inflammatory TGF-β response. Those of ordinary skill in the art recognize that in some embodiments equivalent results can be obtained by directly conjugating an anti-inflammatory protein to the polymer matrix.

In another general aspect, the various embodiments are directed to compositions comprising a hyaluronan polymer matrix, an antibody covalently attached to the hyaluronan polymer matrix (e.g., anti-IL-1β, an anti-IL-6, an anti-TNF-α binding antibody, or combination thereof), and optionally, a linear RGD peptide sequence attached to the hyaluronan polymer matrix, wherein the RGD peptide functions to promote cellular migration and attachment, and the monoclonal antibody functions to inhibit inflammatory response.

In yet another general aspect, the various embodiments are directed to methods of producing an anti-inflammatory composition comprising attaching a ligand binding moiety to the hydrophilic polymer, and optionally, attaching an adhesion peptide to a hydrophilic polymer. In still another general aspect, the various embodiments are directed to methods of producing an anti-inflammatory composition comprising forming a reaction mixture by dissolving hyaluronic acid in phosphate buffered saline; adding 1-ethyl-3-(3-dimethylaminopropyl)carbodiimide, N-hydroxysulfosuccinimide sodium salt, and 4-(dimethylamino) pyridine to the reaction mixture; adding a glycine-arginine-glycine-aspartic acid-serine (GRGDS) (SEQ ID NO: 1) peptide and an antibody to the reaction mixture; and purifying the reaction mixture; wherein the antibody can be a polyclonal or a monoclonal antibody such as an anti-IL-1β, an anti-IL-6, an anti-TNF-α, and combinations thereof.

In yet another general aspect, the various embodiments are directed to methods of treatment comprising administering a composition comprising a hydrophilic polymer, a ligand binding moiety covalently attached to the polymer, and optionally, a cellular adhesion peptide covalently attached to the polymer. The composition may be topically administered directly in a dermal wound, locally administered by hypodermic injection, catheter or endoscopic delivery or direct surgical delivery to an internal lesion, or otherwise delivered by any suitable drug delivery mechanism that will provide local and not systemic application of the composition to a chronic wound. The composition may be used to locally treat a dermal wound, inflammatory bowel disease, rheumatoid arthritis, or any other inflammatory condition characterized by localized inflammation in identifiable tissues.

The hydrophilic polymer may be any biocompatible hydrophilic polymer that can be functionalized with a cellular adhesion peptide and a ligand binding moiety. Suitable polymers include, but are not limited to, GAGs such as dermatan sulfate, chondroitin sulfate, keratan sulfate, heparin, heparan sulfate, and hyaluronan (i.e., hyaluronic acid/hyaluronate). Additional hydrophilic polymers include, for example, agarose, dextran, starch, methyl cellulose, poly(ethylene glycol) ("PEG"), collagen, gelatin, fibrin, fibrinogen, fibronectin, vitronectin, polyhydroxyalkanoates such as polyhydroxybutyrate ("PHB"), polyhydroxyvalerate ("PHV"), copolymers of PHB and PHV, poly(glycolic acid), poly(lactic acid), polycaprolactone, polyanhydrides, poly(ortho esters), poly (amino acids), polyacrylates such as poly(methyl acrylate), and blends thereof.

In various embodiments, the hydrophilic polymer may comprise a blend of different hydrophilic polymers. The blend may comprise two or more different hydrophilic polymers wherein all of the polymers are functionalized with ligand binding moiety and optional adhesion peptide. The blend may alternatively comprise two or more different hydrophilic polymers wherein only one or more of the polymers are functionalized as described herein. In various embodiments, the blends may comprise two or more hydrophilic synthetic polymers, two or more hydrophilic biopolymers, or a mixture of one or more hydrophilic synthetic polymer and one or more hydrophilic biopolymer. As used herein, the term "biopolymer" refers to the class of polymers produced by living organisms, including, for example, polysaccharides, proteins and peptides, DNA and RNA, and glycoproteins. As used herein, the term "synthetic polymer" refers to any man-made polymer produced by synthetic methods.

The hydrophilic polymer blends described herein may be uncrosslinked or in the form of crosslinked gels made in emulsions using any suitable crosslinking strategy known in the art. The crosslinked gels are preferably microgels in emulsions having diameters of a few micrometers.

In one embodiment, the hydrophilic polymer component of the compositions described herein is hyaluronic acid. As used herein, the terms "hyaluronic acid," "hyaluronan," and "hyaluronate" are synonymous and may be used interchangeably. Hyaluronic acid ("HA") is a non-sulfated GAG consisting of alternating residues of D-glucuronic acid and N-acetyl-D-glucosamine. HA is a primary component of the extracellular matrix and is found throughout native tissues, particularly in articular cartilage and skin. The capability of HA to form gels and viscous solutions, un-crosslinked or crosslinked and form hydrogels, and be functionalized on the carboxylic acid group of the glucuronic acid residue, makes it useful in the compositions described herein.

As used herein the term "cellular adhesion molecule" encompasses all protein sequences capable of binding to an integral membrane protein (e.g., an integrin) on a cell, thereby resulting in a cell-protein adhesion. In certain embodiments, a cellular adhesion molecule may comprise specific cellular adhesion peptide sequences including Tyr-Ile-Gly-Ser-Arg ("YIGSR") (SEQ ID NO: 2), and Arg-Gly-Asp and D-Arg-Gly-Asp. See, for example, U.S. Pat. No. 5,120,829, incorporated by reference herein. Cellular adhesion peptides containing the Arg-Gly-Asp and D-Arg-Gly-Asp sequence are capable of promoting cell attachment when they are presented on a matrix or as a substrate. As used herein, the terms "Arg-Gly-Asp" peptide or sequence or "RGD" peptide or sequence refer to a peptide or amino acid sequence having at least one Arg-Gly-Asp-containing sequence which can function as a binding site for an integrin type receptor. See, for example, Ruoslahti et al., "Arg-Gly-Asp: A Versatile Cell Recognition Signal," *Cell*, 44, 517-18 (1986); Ruoslahti et al., "New Perspectives in Cell Adhesion: RGD and Integrins," *Science*, 238, 491-98 (1987); and Ruoslahti et al., "Integrins," *J. Clin. Invest*, 87, 1-5 (1991); all of which are incorporated by reference herein.

It is intended that the term "RGD" peptide in its broadest sense includes a peptide comprising Arg-Gly-Asp or a functional equivalent. For example, an amino acid such as lysine, homoarginine (homoArg) or a mimic of these amino acids is a functional equivalent of arginine. Similarly mimics of Gly and Asp are functional equivalents of glycine and aspartic acid, respectively. Therefore, a peptide including, for example, Lys-Gly-Asp is considered an RGD peptide. As used herein, the term "mimic" means an amino acid or an amino acid analog or homolog that has the same or similar functional characteristic of an amino acid. Thus, for example, an arginine analog can be a mimic of arginine if the analog contains a side chain having a positive charge at physiological pH, as is characteristic of the guanidinium side chain reactive group of arginine. A peptide mimetic or peptidomimetic is an organic molecule that retains similar peptide chain pharmacophore groups as are present in the corresponding peptide. Peptide mimetics also can be functional equivalents of Arg-Gly-Asp.

As used herein, the term "amino acid" in its broadest sense includes naturally occurring proteogenic amino acids and imino acids as well as non-naturally occurring amino acids and imino acids and analogs and mimics thereof. As used herein, the term "proteogenic" indicates that the amino acid can be incorporated into a protein in a cell through well-known metabolic pathways. In view of this definition of an amino acid, one of ordinary skill in the art would know that this definition includes, unless otherwise specifically indicated, naturally occurring proteogenic (L) amino acids, (D) amino acids, chemically modified amino acids including amino acid analogs, naturally occurring non-proteogenic amino acids such as norleucine and chemically synthesized compounds that have properties known in the art to be characteristic of an amino acid.

Cellular adhesion peptides for use in the compositions described herein can be produced synthetically or recombinantly or derived from naturally occurring molecules such as fibronectin or vitronectin, for example. Moreover, an entire adhesion protein such as fibronectin or vitronectin can function as a cellular adhesion peptide in the compositions described herein. In one embodiment, the cellular adhesion peptide component of the compositions described herein is a linear RGD peptide sequence of Gly-Arg-Gly-Asp-Ser ("GRGDS") (SEQ ID NO: 1). The oligopeptide sequence GRGDS can be synthesized according to standard Fmoc solid phase peptide synthesis, however Boc solid phase peptide synthesis, liquid phase peptide synthesis, or other peptide synthesis techniques are applicable. For example, liquid phase peptide synthesis is useful for large-scale production of peptides for industrial and mass-production purposes.

Synthetic cellular adhesion peptides are routinely manufactured in the art. In addition, the smaller size of the peptides allows more binding sites to be attached to a given volume of hydrophilic polymer. These peptides are also much more stable than fibronectin, vitronectin or other larger molecules in solution. Moreover, because they do not carry species-specific immunological determinants, they can therefore be used in both veterinary and human applications. However, cellular adhesion peptides for use in the compositions described herein include larger ECM proteins such as vitronectin, fibronectin or biologically active fragments thereof. In addition, ECM proteins such as vitronectin and/or fibronectin may be blended with one or more hydrophilic polymers wherein at least one of the polymers is functionalized with ligand binding moiety. The hydrophilic polymer/ECM protein blends provide cell adhesion functionality to the compositions described herein, but do not require covalent attachment of a cellular adhesion peptide to the hydrophilic polymer.

As used herein, the term "ligand binding moiety" refers to any moiety capable of binding a ligand, such as a pro-inflammatory mediator. For example, a ligand binding moiety may effectively remove pro-inflammatory mediators from a wound or other local pathological area, and in certain embodiments, attenuate the inflammatory response. Ligand binding moieties include, but are not limited to, polyclonal antibodies or monoclonal antibodies ("mAb") against pro-inflammatory mediators, antibody fragments, aptamers (RNA, DNA, and/or peptide) that selectively bind pro-inflammatory mediators, α-macroglobulins, monospecific cytokine-binding proteins, free cytokine receptors, and receptor fragments capable of binding pro-inflammatory mediators. Ligand binding moieties further include analogs and homologs of mAbs, aptamers, binding proteins, free receptors, and fragments thereof capable of binding pro-inflammatory mediators.

As used herein, the term "antibody fragment" refers to a portion of an intact antibody, such as the ligand-binding or variable region of the intact antibody. Examples of antibody fragments include Fab, Fab, F(ab')$^2$, and Fv fragments; diabodies; single-chain antibody molecules; and multispecific antibodies formed from antibody fragments.

Ligand binding moieties useful in the compositions described herein are capable of specifically binding, and in certain embodiments, neutralizing pro-inflammatory mediators including, but not limited to, cytokines, chemokines, prostaglandins, and complement proteins. For example, specific pro-inflammatory mediators that may be bound by ligand binding moieties include IL-1, IL-6, IL-8, IL-12, IL-18, TNF, MCP-1, IFN-γ, histamine and bradykinin. In some embodiments, the ligand binding moieties for use in the compositions and methods described herein include monoclonal antibodies against IL-1, IL-6 and TNF ("anti-IL-1," "anti-IL-6" and "anti-TNF" respectively). In some embodiments, the ligand binding moieties for use in the compositions and methods described herein include monoclonal antibodies against IFN-γ and TGF-β ("anti-IFN-γ" and "anti-TGF-β").

In various embodiments, the hydrophilic polymer is functionalized with the ligand binding moiety, and optionally, the cellular adhesion peptide. The cellular adhesion peptide and the ligand binding moiety may be covalently attached to the hydrophilic polymer with an effective concentration of adhesion peptide and ligand binding moiety per polymer chain. For example, in one embodiment, a given hydrophilic polymer chain may be functionalized with one ligand binding moiety and four cellular adhesion peptides at various locations along the polymer chain. In other embodiments, a greater number of ligand binding moieties may be covalently attached to the hydrophilic polymer. In still other embodiments, a greater number of cellular adhesion peptides may be covalently attached to the hydrophilic polymer.

In various embodiments, the covalent attachment of the optional cellular adhesion peptide and the ligand binding moiety to the hydrophilic polymer may be accomplished by any suitable chemical methods known in the art. For example, in hydrophilic polymers having pendant carboxylic acid groups (e.g., hyaluronic acid), the cellular adhesion peptide may be covalently attached by reacting the free amine group at the N-terminus of the peptide with a carboxylic acid group on the polymer chain to form an amide bond. The ligand binding moiety may be covalently attached by reacting a pendant amine group on the ligand binding moiety with a carboxylic acid group on the polymer chain to form an amide bond. Furthermore, hydrophilic polymers lacking free carboxylic acid groups may be functionalized with carboxylic acid substituents that function as sites for further functionalization of the polymer by covalent attachment of cellular adhesion peptide and ligand binding moiety thereto. In addition, ligand binding moieties lacking pendant amino groups may be functionalized with amine substituents that function as sites of covalent attachment to the hydrophilic polymer. The various embodiments not limited in this context.

In various embodiments, the covalent coupling of the hydrophilic polymer to the cellular adhesion peptide and the ligand binding moiety is performed by first activating carboxylic acid groups on the polymer with N-hydroxylsulfosuccinimide ("sulfo-NHS") to make them more reactive against the N-terminus amine group on the peptide and a pendant amine groups on the ligand binding moiety. The activated polymer is mixed with peptide and ligand binding moiety in solution and allowed to react forming a composition comprising a hydrophilic polymer, a cellular adhesion peptide covalently attached to the polymer, and a ligand binding moiety covalently attached to the polymer.

In various embodiments, the compositions described herein may be further processed post-synthesis. For example, the compositions may be used to form gels having particular viscosities based, in part, on the molecular weight and the extent of hydration of the hydrophilic polymer. The gels function as a matrix for the controlled application of a ligand binding moiety localized to a pathological site. The gels may be prepared at concentrations of the composition suitable for various applications.

The compositions may also be solidified, particularized and dispersed in a liquid medium to form colloidal suspensions. The compositions may be lyophilized and formed into solid hydratable substrates or tissue engineering scaffolds. The compositions may also be crosslinked to form hydrogels or other constructs using any suitable crosslinking strategy known in the art.

It has been surprisingly found, however, that the geometry of the composition affects its efficacy. When the hydrophilic polymer HA, for example, is crosslinked, it forms a gel similar in consistency to a soft contact lens and millimeters across. The ligand binding moiety is contained in the gel. When applied to a wound, it takes a much longer time for the pro-inflammatory mediators, such as cytokines, to diffuse into the crosslinked gel compared to the time it takes for cytokines to reach cell receptors. In experiments with various embodiments of the polymer, approximately one day was required for cytokines to reach the antibodies in the crosslinked HA matrix.

Figure 2:
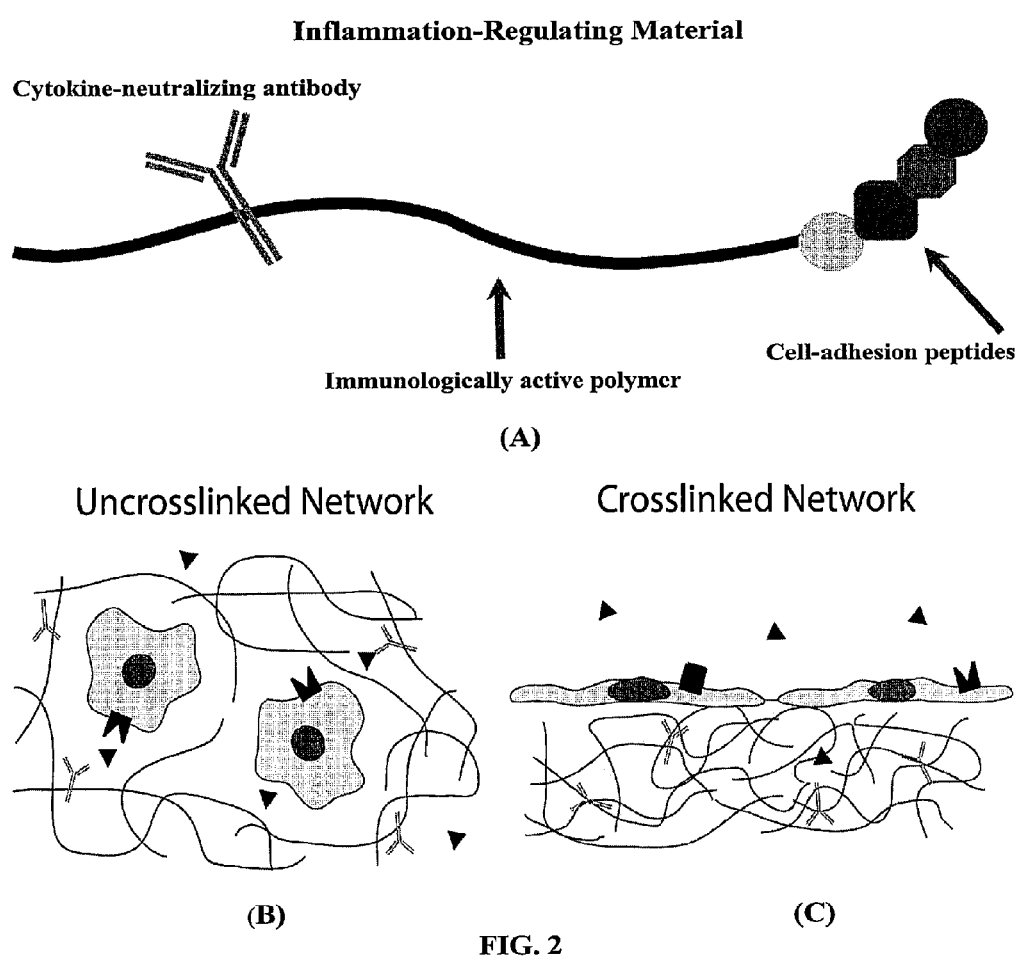
FIGS. 2A-C represent a graphic illustration of one embodiment of the inflammation regulating composition of the present invention (A), and a schematic comparison between the matrix geometry of uncross-linked (B) and cross-linked (C) embodiments of the inflammation regulating composition of the present invention.

Referring to FIGS. 2A-C, one embodiment of the composition is shown schematically (FIG. 2A) to illustrate the differences in the accessibility of the ligand binding moiety to the pro-inflammatory mediators between uncrosslinked and crosslinked polymer matrices. FIG. 2B illustrates the uncrosslinked polymer wherein the antibody bound to the polymer is positioned for relatively unhindered access to the cytokines at the wound site. FIG. 2C, on the other hand, shows how the cells are hindered from interacting with the crosslinked network. While the pro-inflammatory mediators can diffuse into the gel and will be sequestered therein, the slow diffusion rate makes it more likely that the mediators will reach and bind to a cell receptor to trigger the inflammation cascade. A crosslinked polymer gel directly applied to a wound site thus can hinder contact between the antibodies and the cytokines and other pro-inflammatory mediators.

Uncrosslinked polymers or embodiments of crosslinked polymers wherein accessibility is not hindered are preferred to allow the polymer-bound antibody to compete with cell receptors for contact with the pro-inflammatory mediators to effectively neutralize inflammation in vivo, thereby initiating the healing process. For example, a crosslinked polymer may comprise a slurry or a colloidal suspension in the form of beads to promote better diffusion of the composition around the wound site. Crosslinked microgels in emulsions having diameters of a few micrometers should work like the uncrosslinked gels since surface area is high and diffusion times short. In another embodiment, a crosslinked polymer gel may be spread over a larger surface area, for example, on a woven substrate, such as a woven fiber patch, woven mesh, bandage or dressing to bring the composition in intimate contact with the wound site to regulate osmotic pressure at the site and position the antibodies of the composition for ease of contact with the pro-inflammatory mediators in the wound site. Any geometry that positions the ligand binding moiety of the composition in close proximity to pro-inflammatory mediators at the wound site will suffice.

The various embodiments have been described as useful for the treatment of chronic wounds, for example, wounds associated with diabetic ulcers, decubitus/pressure ulcers, venous ulcers, severe burns, ischemia and sickle-cell anemia. However, the compositions described herein as comprising a hydrophilic polymer, a cellular adhesion peptide covalently attached to the polymer, and a ligand binding moiety covalently attached to the polymer are applicable to the localized treatment of any chronic degenerative inflammatory conditions. In dermal or cutaneous wound applications, the compositions described herein may be applied topically, directly to the wound site, as a gel, colloidal suspension, or other suitable viscous delivery substance, and the wound covered with a gauze dressing or other suitable bandage. The compositions described herein may also be used as a component for a bioactive wound dressing, for example, a bandage comprising a wound-contacting portion comprising a composition as described herein. The compositions described herein may also be used to form bioactive wound patches, bioactive wadding, and other bioactive constructs for use in open wounds, lesions or ulcers.

The compositions described herein may also be used to treat arthritis (e.g., osteoarthritis or rheumatoid arthritis). In arthritic applications, the compositions described herein may be injected directly into the cartilage or synovial fluid of a joint. The compositions described herein may also be incorporated into tissue engineering scaffolds for surgical implantation into a joint in order to locally mitigate chronic inflammation and promote tissue regeneration. In arthritic applications, the cellular adhesion peptide and hydrophilic polymer allow for regenerative growth of arthritic tissue while simultaneously attenuating the inflammation that characterizes arthritic conditions The compositions described herein may also be used to treat inflammatory bowel disease ("IBD") (e.g., Crohns disease or ulcerative colitis). In IBD applications, the compositions described herein may be delivered to the lumen of the gastrointestinal tract by any suitable means known in the art. For example, the compositions may be delivered to the large intestine via suppository, catheter or endoscope.

The various embodiments also provide a method of treatment. The method comprises administering a composition comprising a hydrophilic polymer, a cellular adhesion peptide covalently attached to the polymer, and a ligand binding moiety covalently attached to the polymer. Administration of the composition may be by any suitable means known in the art, including, but not limited to, topical application of gels, ointments, salves, lotions, sprays, creams, balms, or powders comprising the composition; intestinal application (via the rectum) of suppositories or gels; or subcutaneously by injection into a site. In addition, the composition may be administered by applying a wound dressing or bandage comprising the composition, or by implanting a construct (e.g., a regenerative tissue engineering scaffold implanted via surgical or non-surgical methods) comprising the composition.

In any respective application, the compositions and methods described herein provide an important improvement in the treatment of chronic degenerative inflammatory conditions by enhancing cell growth and tissue regeneration while simultaneously inhibiting the inflammatory response. When a ligand binding moiety and a cellular adhesion peptide are covalently attached to a hydrophilic polymer, the ligand binding moiety functions to inhibit signaling due to the most active pro-inflammatory mediators (such as the cytokines IL-1, IL-6 and TNF), and the polymer-adhesion peptide matrix promote tissue regeneration. The compositions have multiple levels of biological activity and represent a significant advance in the treatment of chronic degenerative inflammatory conditions. Moreover, the compositions described herein function to treat chronic inflammatory conditions in a localized fashion. Therefore, the compositions and methods described herein minimize or eliminate any systemic effects that may otherwise be present if chronic inflammatory conditions are treated with non-localized, or free ligand binding moieties.

The following examples are intended to more clearly illustrate aspects of the compositions and methods described herein, but are not intended to limit the scope thereof.

EXAMPLES

Example-1

Synthesis of HA Functionalized with RGD Peptide and Anti-IL-1, Anti-IL-6 and Anti-TNF Compositions comprising HA functionalized with RGD peptide and anti-IL-1β, anti-IL-6 and anti-TNF-α were synthesized.

MATERIALS: Hyaluronic acid (HA, ~1.6×10$^6$ g/mol), N-hydroxysulfosuccinimide sodium salt ("sulfo-NHS"), N-(3-dimethylaminopropyl)-N'-ethylcarbodiimide hydrochloride ("EDC"), and 4-(dimethylamino)pyridine ("4-DMAP") were purchased from Sigma-Aldrich (3050 Spruce St., St. Louis, Mo. 63103) and used as received. Acryloyl-PEG-N-hydroxysuccinimide (ARCL-PEG-NHS, 3.4 kDa) was purchased from Nectar Therapeutics. The oligopeptide sequence GRGDS was synthesized according to standard Fmoc solid phase peptide synthesis. The Fmoc-protected amino acids, N,N'-diisopropylcarbodiimide ("DIC"), and N-hydroxybenzotriazole ("HOBt") were purchased from EMD Chemicals Inc. (San Diego, Calif.) and used as received. Anti-mouse-IL-1β from purified rat monoclonal IgG1 was purchased from R&D research (Minneapolis, Minn.).

In order to couple both GRGDS and anti-IL-1β to HA, the carboxylic acid groups of the glucuronic acid residue of HA were activated by reacting HA with EDC, 4-DMAP, and sulfo-NHS in phosphate-buffered saline (PBS) solution for overnight, for 12 hours. HA (10 mg, 6.25 nmol) was dissolved in phosphate buffer saline (pH ~7.4) (2 ml). EDC (120 μg, 625 nmol), Sulfo-NHS (217 μg, 1 μmol), and 4-DMAP (10 μg) were added as solids to the HA solution and allowed to dissolve and react for 12 hours. The molar ratios of the reagents were adjusted so that, accounting for the reactivity of sulfo-NHS, five carboxylic acid groups per HA chain were expected to be activated.

Carbodiimide-Mediated Coupling of Anti-Human IL-1β to HA. The HA-NHS active ester is a versatile precursor for bioconjugation with primary amines. Anti-human IL-1β (9.4 mg, 62.5 nmol) was added to the activated HA solution. The reaction proceeded at room temperature for 4 hours. The solution was purified by dialysis with continuous stirring in a double sided magnetic Biodialyzer (Nestgroup, Inc) with a 300 kDa MWCO cellulose acetate membranes (Nestgroup, Inc) for 4-6 hours against phosphate-buffered saline (pH 7.4).

Synthesis of RGD Conjugate.

The GRGDS peptide was dissolved in anhydrous dimethylformamide; ("DMF") containing 4 molar excess of triethyl amine ("TEA"). ACRL-PEG-NHS was also dissolved in anhydrous DMF and immediately after, mixed with 1.1 molar excess of peptide. After incubating for 3 hr at room temperature, ACRL-PEG-GRGDS was precipitated twice in cold anhydrous ether and dried in a vacuum oven overnight at room temperature. The peptide coupling reaction and molecular mass of the product was monitored by matrix-assisted laser desorption and ionization time-of-flight mass spectrometry ("MALDI-TOF MS").

Following thorough removal of the acetone, the activated HA was re-dissolved in PBS, mixed with a 50-fold molar excess of GRGDS peptide and 10-fold molar excess of anti-IL-1β and allowed to react for 4 hours. The reaction solution was purified by dialysis with continuous stirring in a double sided magnetic Biodialyzer with a 300 kDa molecular weight cut-off ("MWCO") cellulose acetate membrane for 4-6 hours against PBS (pH 7.4) in order to remove unattached antibody. Finally, the RGD-HA-anti-IL-1β product was twice precipitated using ammonium sulfate in order to remove residual contaminants. The supernatant was removed and the purified composition was re-suspended in 25 μl PBS and frozen until further use.

The synthesis protocol described above utilized anti-IL-1β as the ligand binding moiety. However, one of ordinary skill in the art would appreciate that the protocol may be readily extended to any ligand binding moiety having, or modified by known procedures to have, a pendant amine group (e.g., antibodies such as anti-IL-6 and anti-TNF-α).

Example-2

Characterization of the RGD-HA-Anti-IL-1β Composition

Figure 3:
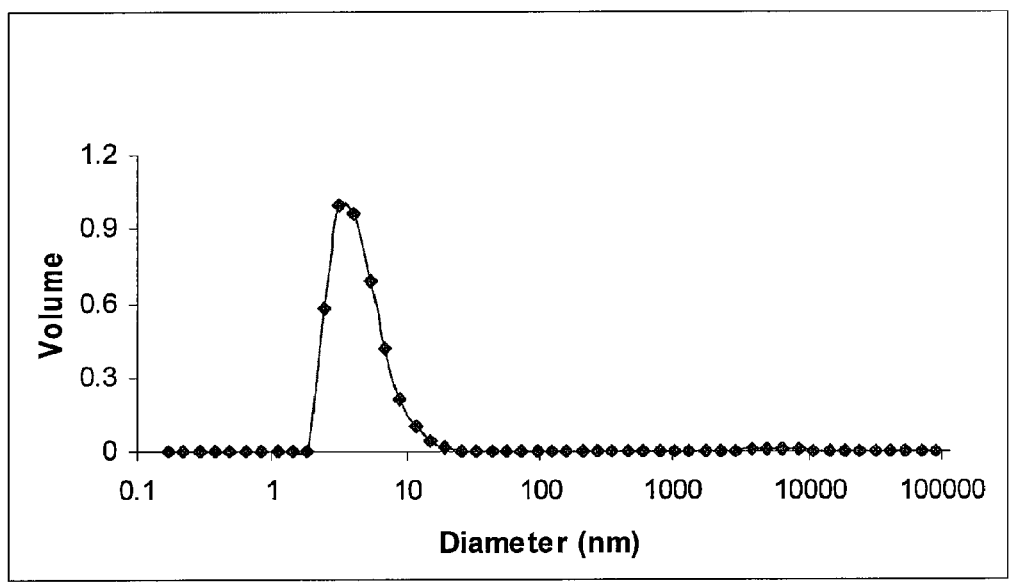
FIG. 3 is a graph illustrating dynamic light scattering data indicating the purity of a composition comprising hyaluronic acid functionalized with covalently attached anti-IL-1β.

The RGD-HA-anti-IL-1β compositions of Example-1 were characterized by dynamic light scattering, which characterizes materials based on their diffusion constant in solution and is extremely sensitive to the state of aggregation or crosslinking in a sample. Purity of the composition is verified by measuring a single peak in the dynamic light scattering spectrum. FIG. 3 is a graph illustrating dynamic light scattering data indicating the purity of the composition. As can be seen from FIG. 3, any residual unbound antibody is removed by the dialysis purification as indicated by the single peak in the dynamic light scattering spectrum.

Example-3

Characterization of RGD-HA-Anti-IL-1β Activity Against IL-1β

The biological activity of the RGD-HA-anti-IL-1β compositions of Example-1 were characterized by quantifying the intracellular translocation of nuclear factor-κB ("NF-κB") in THP-1 macrophages. The signaling of most pro-inflammatory cytokines involves the NF-κB pathway in which NF-κB is maintained in an inactive state in the cellular cytoplasm by an inhibitor protein I-κB until it is dislodged, allowing NF-κB to migrate to and enter the nucleus where NF-κB initiates transcription events that mount an inflammatory response. This assay is commonly performed with THP-1 cells that have been differentiated with phorbol 12-myristate 13-acetate ("PMA") and adopt a macrophage-like phenotype. The intensity of the response to pro-inflammatory cytokines in these cells has been shown to be a monotonic function of the concentration of active cytokine in solution. Cytokine inactivation by antibodies or other ligand binding moieties leads to lower translocation of NF-κB into the nucleus, which can be quantified by imaging cytometry.

THP-1 Differentiation.

THP-1 monocytes were obtained from the American Type Culture Collection (Manassas, Mass.). Cells were cultured between 0.5-7×10$^5$ cells/ml in RPMI 1640, purchased from Cellgro, containing 10% fetal calf serum ("FCS"), L-glutamine, 100 U/ml Penicillin, and 100 µg/ml Streptomycin, and maintained in 37° C. and 5% $CO_2$. Monoclonal anti-human IL-1β antibody and IL-1β were purchased from R&D Systems Inc. (Minneapolis, Minn.). Anti-NF-κB (P65) mouse monoclonal antibody (F-6) was purchased from Santa Cruz Biotechnology (Santa Cruz, Calif.). Secondary antibody (goat anti-mouse IgG-conjugated with Alexa 680 or Alexa 488) and Hoechst 33342 were purchased from Molecular Probes (Carlsbad, Calif.). Phorbol 12-myristate 13-acetate (PMA) was purchased from Sigma (St. Louis, Mo.). Reagents were reconstituted and stored according to the manufacturer's instructions.

Cell Stimulation, Fixation, and Staining for Image Analysis.

THP-1 cells were cultured in a 96-well plate with an initial cell density of 15,000/well. Each well was treated with RPMI 1640 media containing 20 nM of PMA for 48 hrs in 37° C. followed by 24 hrs of recovery in fresh media. Cells were stimulated for 30 minutes according to one of four experimental conditions: (1) untreated; (2) treated with 100 ng/ml IL-1β; (3) treated with 100 ng/ml IL-1β and 100 µg/ml anti-IL-1β; and (4) treated with 100 ng/ml IL-1β and 100 µg/ml HA-anti-IL-1β.

Following experimental treatment, supernatants were gently aspirated and the cells were fixed in 2% paraformaldehyde in plates for 10 minutes. They were then washed once in PBS and permeabilized for 10 minutes with permeablizing buffer. They were incubated in the presence of 1 µg/ml anti-NF-κB antibodies for 1 hour. Cells were treated with detergent for 10 minutes followed by 1 hour incubation in the presence of 2 µg/ml secondary antibodies and 1 µg/ml solution of Hoechst 33342. The cells were then treated with detergent for 10 min and 200 µl of PBS were added to each well. Plates were covered and stored at +4° C. until analysis.

Data Acquisition and Analysis.

The ArrayScan VTI imaging cytometer (Cellomics) is an automated fluorescent imaging microscope that acquires spatial information of the fluorescently labeled component in cells. The system scans several fields in each individual well and analyzes the images of each field according to a defined algorithm. The system will acquire enough images of the fields in each well until a predefined number of cells has been identified and analyzed. The ArrayScan was equipped with emission and excitation filters for different fluorescent signals emitted by Hoechst 33342, Alexa 488, and Alexa 680. Data were Acquired and analyzed by ArrayScan Compartmental Analysis Bioapplication version 5.5.1.3 and HCS viewer (Cellomics).

Figure 4:
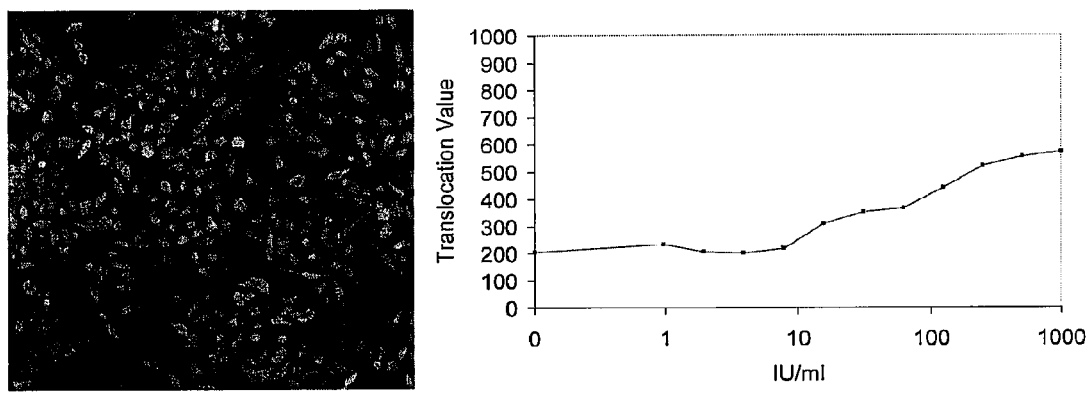
FIG. 4 presents a cytometry image and the translocation of nuclear factor-κB assay dose-response curve for THP-1 macrophage cells against IL-1β.

The translocation assay reports the ratio of NF-κB in the nucleus to that in the cytoplasm, adjusted for background fluorescence intensity, so a larger value from the assay corresponds to a stronger response. This has been shown to be an accurate, quantitative measure of the intensity of incipient inflammatory responses in cultured cells. See Vakkila et al., "Imaging analysis of STAT1 and NF-kappa-B translocation in dendritic cells at the single cell level," *J. Immunol Methods*, 294, 123-134 (2004). FIG. 4 presents a cytometry image and the dose-response curve for THP-1 cells against IL-1β. A sigmoidal curve was observed, with an inflection point around 10 ng/ml. Based on these data, it was concluded that IL-1β doses of 100 ng/ml would produce strong NF-κB translocation that could still be readily inhibited by molecules with a reasonable affinity for the cytokine.

Figure 5:
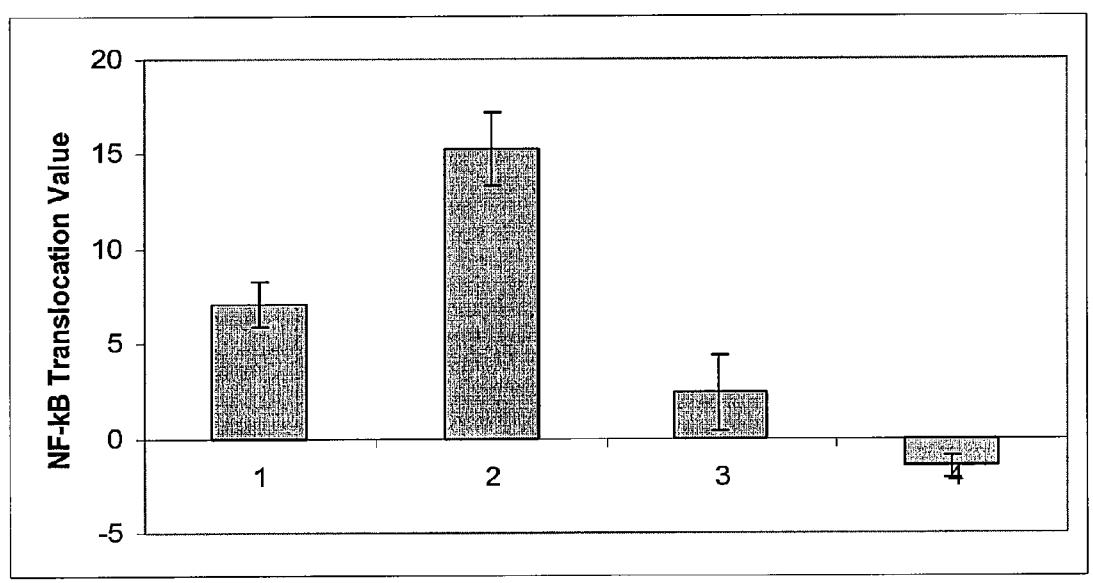
FIG. 5 is a bar graph illustrating translocation of nuclear factor-κB assay results for THP-1 macrophages treated with IL-1β and hyaluronic acid polymer functionalized with RGD peptide and anti-IL-1β for (1) untreated tissue, (2) tissue treated with IL-1β, (3) tissue treated with IL-1β and anti-IL-1β, (4) tissue treated with HA-anti-IL-1β.
Figure 6:
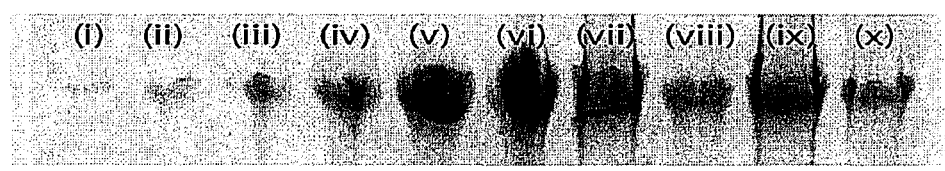
FIG. 6 is PAGE analysis of HA-mAb conjugates. Lanes (i)-(v) were used to calibrate densitometric analysis of the bands to provide quantitative measures of HA concentration. Independent measurements of mAb concentrations in each sample using a modified ELISA method (data not shown), were used to calculate the degree of mAb functionalization on each HA chain (14% under these conditions). Lanes (vi)-(x) represent: (vi) 0.1% HA, (vii) 1×HA-mAb conjugate, (viii) 0.1×HA-mAb conjugate, (ix) 1×HA+mAb mixture, (x) 0.1× HA+mAb mixture.
Figure 7:
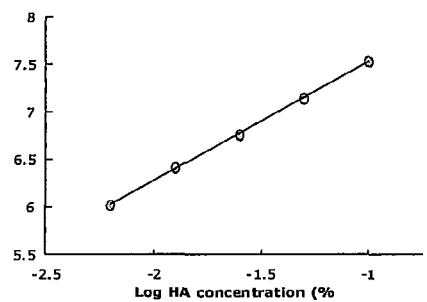
FIG. 7 is a graph of the reverse log of HA concentration in the analysis illustrated in FIG. 6.
Figure 8:
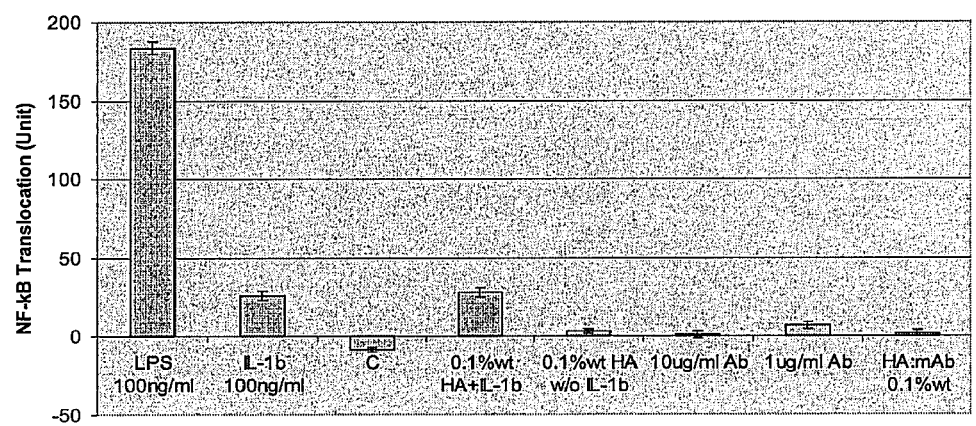
FIG. 8 is a bar graph of the NF-κB translocation measured in THP-1 macrophages challenged with LPS, IL-1β, no stimulus (C), mixtures of HA and IL-1β, HA only, and IL-1β, with doses of mAb at 10 µg/ml and 1 µg/ml and the HA-mAb at 0.1 wt %.

FIG. 5 is a bar graph illustrating the translocation assay results for IL-1β. The baseline translocation value for untreated THP-1 cells was 7.1±2.2. Cells stimulated with 100 ng/ml IL-1β had translocation values of 15.0±1.9 while cells that were treated with the same dose of IL-1β and a 10-fold molar excess of anti-IL-1β had translocations values of 2.9±2.0. Addition of 100 µg/ml HA without anti-IL-1β showed no significant effect on the cellular response to the same dose of IL-1β as was given the positive control samples (data not shown), but cells exposed to IL-1β and a 10-fold excess of HA-anti-IL-1β exhibited essentially no NF-κB translocation, indicating that (1) the HA-anti-IL-1β conjugates provide significant inhibition of IL-1β signaling, and (2) that little reduction in anti-IL-1β binding affinity for IL-1β occurred when it was covalently attached to HA.

Example-4

MATERIALS. Neutralizing monoclonal antibodies against IL-1β, IL-6, and TNF-α derived from rat IgG1 in a mouse host will be used (R&D Systems), but the synthesis and purification will otherwise be identical to those described above. There is a 95% homology between mouse and rat TNF-α, a 90% homology between mouse and rat IL-1β, and an 85% homology between mouse and rat IL-6, and good cross-reactivity is reported from the supplier.

Monoclonal antibodies (mAb) were coupled to hyaluronic acid using carbodiimide chemistry as described in Example-1 above. The mAb concentrations were measured using polyacrylamide gel electrophoresis (PAGE) and a modified enzyme-linked immunosorbent assay (ELISA). Solutions of known HA concentrations were analyzed using PAGE, stained with Alcian Blue, and analyzed using quantitative image analysis. By independently measuring the mAb concentration using ELISA (data not shown), a molar mAb:HA ratio of 14% was calculated. The concentration of mAb in the gels can be controlled by changing the HA concentration. FIG. 6 shows the PAGE analysis of the HA-mAb conjugates. Lanes (i)-(v) were used to calibrate densitometric analysis of the bands to provide quantitative measures of HA concentration. Independent measurements of mAb concentrations in each sample using a modified ELISA method were used to calculate the degree of mAb functionalization on each HA chain (14% under these conditions). Lanes (vi)-(x) represent: (vi) 0.1% HA, (vii) 1×HA-mAb conjugate, (viii) 0.1×HA-mAb conjugate, (ix) 1×HA+mAb mixture, (x) 0.1×HA+mAb mixture. FIG. 7 shows the calibration curve for PAGE analysis of HA concentration fit by $y=361.31x-2.3587$ ($R^2=0.9921$).

The neutralizing activity of antibodies against IL-1β that were covalently attached to HA was measured using NF-κB translocation assay. One of the final steps in the signal transduction pathway of many pro-inflammatory cytokines is the liberation of NF-κB from the inhibitory molecule I-κB that prevents its passage through the nuclear membrane. Measuring the ratio of NF-κB in the nucleus to that in the cytoplasm provides a quantitative measure of an incipient response to mediators of inflammation. Using imaging cytometry, THP-1 macrophages were challenged with IL-1β, and NF-κB was labeled immunofluorescently. The translocation of NF-κB was measured in >2000 adherent cells per experimental condition that were stained with Hoechst to identify the nucleus.

FIG. 8 shows NF-kB translocation data that indicates that the HA-mAb conjugates are still capable of neutralizing IL-1β in vitro. The NF-κB translocation data was measured in THP-1 macrophages that had been challenged with LPS, IL-1β, no stimulus (C), mixtures of HA and IL-1β, HA only, and IL-1β, with doses of mAb at 10 μg/ml and 1 μg/ml and the HA-mAb at 0.1 wt %. Increases in translocation are associated with increases in incipient inflammatory responses.

Example-5

The biological activity of HA-RGD-mAb conjugates was tested subcutaneously in healthy rats. The RGD peptide was covalently attached to the HA-mAb gels via a poly(ethylene glycol)-acryoyl chloride linker. Incisions on the backs of shaved, anesthetized animals were made, and the skin was raised to expose the underlying tissue. The fascia was damaged by scraping to increase the recruitment of mononuclear cells capable of participating in a local inflammatory response. The gels were delivered to the site, which was sutured closed. After 4 days, the rats were sacrificed and samples were collected that include the injury site and underlying muscle. Adjacent tissue sections were stained with Masson's trichrome and antibodies against CD68, CD163, and CCR7. The cell-surface marker CD68 was used to identify macrophages at the injury site. The basic phenotype of these cells was characterized using CD163, which is associated with an M2 phenotype, and CCR7, which is associated with an M1 phenotype.

The results of testing gels that only contained mAb against IL-1β or TNF-α were not found to inhibit macrophage invasion or phenotype significantly (data not shown). Gels containing 100 μg mAb were delivered subcutaneously in 250 μl of HA-RGD-mAb gels. These results are compared against control samples of HA-RGD (no mAb), and no significant differences between these treatments were observed. At 4 days, significant invasion of macrophages was evident, and the early stages of repair were initiated. Interestingly, cells that stained positively for CCR7 in these samples were less abundant than sites treated with saline solution. Without wishing to be bound by theory, this result may indicate that the HA matrix itself may influence macrophage phenotype but that targeting a single cytokine may not effectively alter the inflammatory response. It should be understood that the preliminary experiments reported herein on healthy rats would not necessarily be the same as the results in experiments on healing-impaired animals or humans with chronic wounds because the latter two groups, as explained previously herein, do not exhibit the same wound healing behavior.

Example-6

Figure 9:
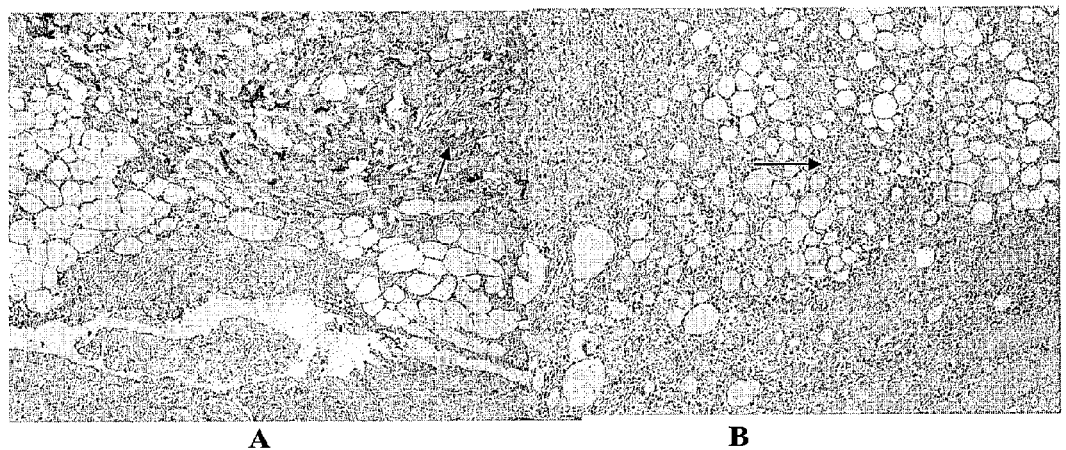
FIGS. 9A-B are images of tissue sections from sites treated with HA-RGD-anti-IL-1β/anti-TNF-α (A) and HA-RGD control (B). Muscle tissue is visible at the bottom of both fields, above which the skin was lifted and the fascia damaged. The mAb+ site has significantly fewer invading macrophages in the repair area (shown by an arrow) relative to the HA-RGD control, and fewer of these stain positively for CCR7 than in the saline-treated site, suggesting that the gels are inhibiting the M1 phenotype. Furthermore, the repair areas treated with the HA-RGD-mAb gels showed delayed healing relative to the HA-RGD-treated controls. This suggests that the gels are biologically active, but the inhibition of inflammation is too strong, which is preventing healing.

Gels containing mAb against both pro-inflammatory cytokines IL-1β and TNF-α were tested in vivo. Following the same protocol used in Example-5, samples were again harvested at 4 days. However, there was an obvious difference in the gross qualities of the mAb-containing site and the HA-RGD sample used as a negative control. The mAb-containing site displayed poor healing during the first four days and had a noticeable build-up of fluids. Histological analysis of these tissues was consistent with these observations. FIGS. 9A and B show tissue sections from sites treated with HA-RGD-anti-IL-1β/anti-TNF-α (9A) and HA-RGD control (9B) from Example-6. Muscle tissue is visible at the bottom of both fields, above which the skin was lifted and the fascia damaged. The tissue between the muscle and dermis was loosely connected in the mAb-containing site, and there was a significant decrease in macrophage invasion relative to the HA-RGD control.

It is interesting to note that the macrophages that were present in the mAb-containing sample were clustered, while those in the negative control were more evenly distributed in the healing tissue. As shown in FIG. 9A, these cells tend to stain positively for CCR7, suggesting that macrophages are establishing an inflammatory microenvironment in these clusters, but that overall there is a significant variation in the course of the inflammatory response. The mAb-containing site has significantly fewer invading macrophages in the repair area (shown by an arrow) relative to the HA-RGD control, and fewer of these stain positively for CCR7 than in the saline-treated site, showing that the gels are likely inhibiting the M1 phenotype. Furthermore, the repair areas treated with the HA-RGD-mAb gels showed delayed healing relative to the HA-RGD-treated controls. This suggests that the gels are biologically active, but the inhibition of inflammation is too strong, which is preventing healing. Different doses of mAb may be tested in healthy and healing-impaired animal models, such as rats, and eventually in humans, to determine an optimal level of cytokine inhibition. The optimal dosage may depend on the underlying cause of the wound, its severity and the patient's general condition.

Preliminary efforts at quantifying the data yielded the following results [expressed as {number of CCR7+ cells}/{number of CD68+ cells} (% of CCR7+ cells)]:
HA-RGD-mAb: 18/182 (10%) HA-RGD w/o mAb: 57/491 (12%) Saline: 133/282 (47%).

These early results indicate that the combination of anti-IL-1β and anti-TNF-α in an HA matrix reduces the invasion of monocytes/macrophages and inhibits the development of the M1 phenotype. From the evaluation of the site, a combination of extensive cytokine neutralization appears to inhibit healing 4 days post-surgery. While the inhibition of healing is not the goal of the composition, these results indicate that the HA-RGD-mAb gels are capable of altering the inflammatory response in healthy animals. It is believed that optimal levels of mAb in an HA gel will improve healing, especially in healing-impaired animals.

Sprague-Dawley rats are an accepted, although imperfect small-animal model in the study of inflammatory responses. These rats have a complement of specialized leukocytes similar to those in humans, and many of the same chemokines and cytokines that participate in mounting an inflammatory response. Therefore, studies on inhibiting the central pro-inflammatory cytokines IL-1β and TNF-α will provide useful information in developing these gels for use in humans.

The effects of IL-1β on macrophages include initiation of cyclooxygenase-2 and vascular endothelial growth factor, thus supporting host defenses and angiogenesis. See Dinarello C. A., "Interleukin-1 Family," The Cytokine Handbook. 4th ed. London: (in Thomson A W, Lotze M T, editors) Elsevier Science Ltd., p. 643-668 (2003). TNF-α participates in coagulation and host responses to infections and also promotes the production of IL-1β. Together, TNF-α and IL-1β are central mediators of the inflammatory response. The focus of the following experiments is to determine the effects of HA-RGD-mAb conjugates that inhibit these cytokines separately or together in wound healing. The effects on invading macrophages in vivo and correlations with changes in tissue repair will be measured.

Treatment of the rats with streptozotocin (STZ) will induce diabetes and result in impaired neutrophil function, delayed macrophage invasion, and inhibition of cellular proliferation and angiogenesis. Furthermore, STZ-treated rats have been shown to upregulate NF-κB and intercellular adhesion molecule-1 expression, and extensive macrophage infiltration has been measured following ischemia-reperfusion. See Wang Y. et al., "Decreased peripheral nerve damage after ischemia-reperfusion injury in mice lacking TNF-alpha," Journal of the neurological sciences, 267(1-2):107-111 (Apr. 15, 2008). While the response to STZ treatment will vary for each rat, we expect this cohort to have delayed but intensified inflammatory responses following injury.

Control Experiments

Example-7

Control samples will include undamaged tissue, treatment with saline solution, treatment with HA-RGD, and treatment with unconjugated antibodies alone. Treatment with HA-RGD without any antibodies will provide measures for understanding the effects of inhibiting cytokines at the injury site, while treatment with saline will provide an understanding of the intrinsic effects of the HA-RGD gels. Finally, the treatment with unconjugated antibodies will provide a test of the relative efficacy of attaching them to the HA matrix. Recovered tissue sections will be sectioned and analyzed by histology and immunohistochemistry. The markers for macrophage responses will be overall determination of invasiveness, assessed by mapping the number and spatial distribution of these cells in the injury site, and macrophage phenotype. Macrophage phenotype is assessed through immunohistochemistry; this will provide a focused view of cellular response at the injury site. Positive staining is currently used for CD68 as a pan-macrophage marker, CD163 for the M2 phenotype, and CCR7 for the M1 phenotype.

The first step in characterizing the biological activities of cytokine-inhibiting gels is being done through subcutaneous implantation of HA-RGD-mAb gels in healthy rats. Preliminary studies were done using 250 μl of gel containing 100 μg of mAb against IL-1β and TNF-α. Antibody doses of 1-100 μg of a single mAb or 2-200 μg of two mAb, or 3-300 μg of three mAb may be sued.

The experiments on subcutaneous implantation of HA-RGD-mAb gels done in healthy rats will be repeated in STZ-treated rats to provide an early indication of their effects on subjects with impaired healing responses. STZ-treated rats are expected to have more intense inflammatory responses during the early stages of wound healing and delayed healing trajectories, but STZ-treated rats are expected to show improvements in healing, such as the extent of collagen deposition and the number of blood vessels in the injury site.

Three strategies may be used to optimize the efficacy of the composition of the invention. The first is to incorporate a logarithmic increase in the highest anti-IL-1β/anti-TNF-α concentrations in the gel formulation. Very high concentrations of mAb may be required in certain applications to compete with cell receptors for cytokines. The second is a logarithmic decrease in the lowest anti-IL-1β and anti-TNF-α concentrations. Without wishing to be bound by theory, very high concentrations of mAb may act to increase the local concentration of these cytokines at the injury site, and a lower mAb concentration would compete effectively with cell receptors while permitting natural clearance processes to occur. Finally, the gel formulation may be changed to include mAb against interleukin-6 or interferon-γ. Both cytokines represent alternate pro-inflammatory targets for the ligand binding moiety of the composition.

In an alternative embodiment, mAb may be covalently attached to non-degradable gels based on crosslinked poly(ethylene glycol) ("PEG"). PEG gels lack the intrinsic of biological activity of HA but will provide a stable delivery vehicle at the injury site, and it may be readily combined with HA. The combination of PEG and HA will prevent systemic release of the HA-mAb composition, which could negatively impact the patient's immune system.

In various embodiments of the composition, it may be formulated so that the HA-RGD-mAb gels provide significant inhibition of the inflammatory response at the lowest possible dose of mAb.

It is expected that there will be improvements in the healing of full-thickness wounds in STZ-treated rats at higher mAb doses than in healthy rats because of the unregulated nature of the inflammatory response in diabetic animals. These improvements will be manifested as increased rates of re-epithelialization, re-establishment of the vascular system, and recapitulation of connective tissue. In healthy rats, it is expect that there will be improvements in healing at lower mAb concentrations but possibly not at higher concentrations because a healthy inflammatory response in the healing process is likely near optimal in healthy animals. The mechanical properties of tissues are expected to improve with healing outcomes, especially in the STZ-treated rats.

In various embodiments of the methods of treatment, the composition may be applied and then re-applied every two days in certain healing resistant wounds. Alternatively, crosslinked gels may be processed into forms that resemble wound dressings using freeze-drying techniques. Formulating the composition into pre-packaged wound dressings is particularly useful for clinical applications of these materials.

Example-8

Binding Affinity Measurements

The Octet system (ForteBio Corp.) was utilized to measure HA-mAb binding affinity for IL-1β. The Octet measures the reflection coefficient as broadband visible light propagates to the end of a fiber optic. Changes in the refractive index at the fiber optic-solution interface result in a wavelength-dependent shift in the maximum of the reflection coefficient. Association and dissociation curves are fit to equations of the following form:

$$R(t) = R_0 + \Delta R \{1 - \exp[-k_{on}(t - t_{on})]\}$$

$$R(t) = R_0 + \Delta R \exp[-k_{off}(t - t_{off})]$$

where $R(t)$ is the reflection coefficient at time t, $R_0$ is the baseline value of the reflection coefficient, $\Delta R$ is the total change in response, $k_{on}$ is the association rate constant, $t_{on}$ the time at which the sensor is placed in solution containing the analyte, $k_{off}$ is the dissociation rate constant, and $t_{off}$ is the time at which the sensor is placed in pure buffer solution. The values for $k_{on}$ and $k_{off}$ are determined from curve fitting, and their ratio provides a measurement of $K_D$. Protein A sensor tips were hydrated in sample diluent (0.02% Tween 20, 150 mM NaCl, 1 mg/ml BSA, 10 mM phosphate buffered saline, and 0.05% sodium azide) supplied by ForteBio for at least five minutes before the experiment. All the samples were diluted in buffer. Mouse anti-human IL-1β monoclonal antibody was diluted to 10 μg/ml, and the HA-mAb sample was diluted to the equivalent concentration of antibody. Human IL-1β was diluted to desired concentration in sample diluent. The experimental setup is as followed in the following specific sequence: sample diluent 5 minutes (baseline), Antibody or HA-mAb solution 60 min (loading), sample diluent 10 min (wash), sample diluent 10 min (wash), sample diluent 15 min (baseline), IL-1β solution 40 min (association), and sample diluent 60 min (dissociation). The results were analyzed by the ForteBio analysis program that generated the best-fit binding isotherm and the association rate $k_{on}$ and dissociation rate $k_{off}$ were calculated from the isotherm.

Example-9

The hydrophilic polymer of the composition may be carboxymethylcellulose (CMC). The CMC was "ultra-high molecular weight" material obtained from Sigma-Aldrich. Two carboxymethylcellulose-monoclonal antibody (CMC-mAb) conjugates were made by known procedures. The putative average molecular weight was greater than 1×10^6 g/mol and conjugation and purification were done the same as for hyaluronic acid conjugates. The CMC-mAb conjugates were tested using the ForteBio binding affinity assays described above. The results follow:

Rat anti-mouse IL-1beta mAb KD=41 pM
Rat anti-mouse IL-1beta mAb conjugated to carboxymethylcellulose KD=38 pM
Rat anti-mouse TNF-alpha mAb KD=37 pM Rat anti-mouse TNF-alpha mAb conjugated to carboxymethylcellulose KD=215 pM The error bars on KD are probably about +/−5 pM. Because this is a different antibody clone than used in Example-1, the KD of the unconjugated mAb was expected to be different. Baseline calibrations were different, so these numbers may be lower. It is believed that CMC does not inhibit mAb binding to IL-1β but does interfere somewhat with TNF-α binding. However, good binding kinetics were observed. Therefore, it is not completely interfering with TNF-α binding.

Figure 10:
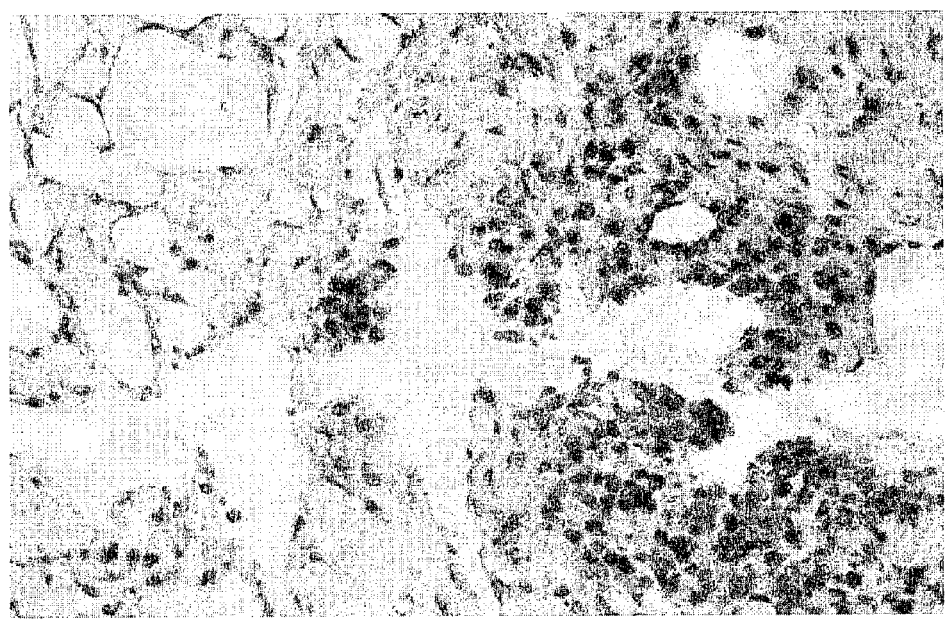
FIG. 10 is a photograph of a saline controlled tissue section.
Figure 11:
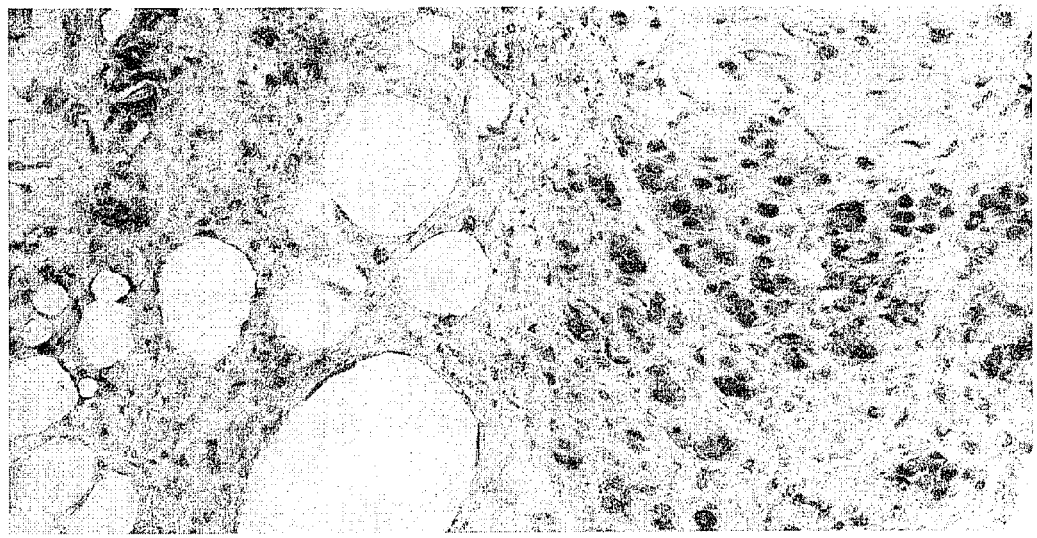
FIG. 11 is a photograph of a HA-RGD tissue section.
Figure 12:
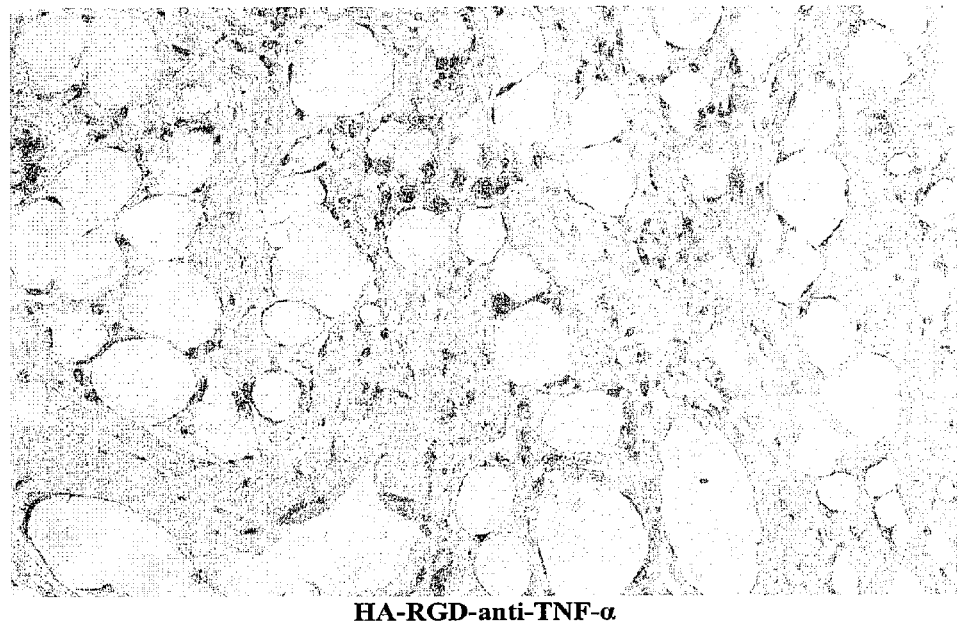
FIG. 12 is a photograph of a HA-RGD-anti-TNF-α tissue section.
Figure 13:
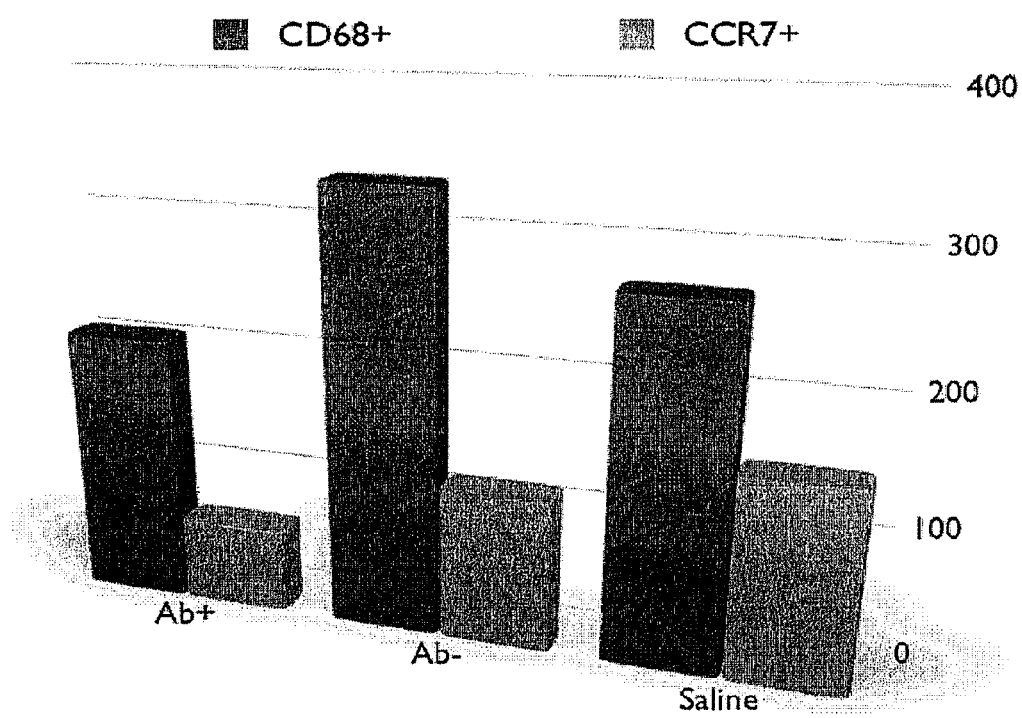
FIG. 13 is a bar chart showing the summary of anti-TNF data

FIGS. 10-12 show representative images from surgical sites treated with saline (FIG. 10), HA-RGD (FIG. 11), and HA-RGD (FIG. 12) coupled with anti-TNF-α. The site was stained for CD68, which is a general macrophage marker. A significant decrease was observed in the number of macrophages in the HA-RGD-anti-TNFa site relative to the site treated with saline and that treated only with HA-RGD. This supports the approach of neutralizing TNF to decreasing macrophage invasion. Referring to FIG. 13, a bar graph shows the summary of anti-TNF-α data based on multiple sites (CD68 and CCR7+ cells represent M1 macrophages).

Example-10

Proposed Animal Experiments

Wound healing experiments on healthy rats will be performed. Full-thickness wounds will be prepared in healing-impaired rats. Rats treated with streptozotocin, which selectively kills cells that express high levels of the glucose transport protein GLUT2, develop symptoms similar to diabetes. Their wounds heal poorly and respond positively to topically applied PDGF and TGF-α as do wounds in diabetic humans. The model is one standard for testing the efficacy of new therapies for wound healing.

Monoclonal antibodies against IL-1β, IL-6, and TNF-α derived from rat IgG in a mouse host will be used (R&D Systems), but the synthesis and purification will otherwise be identical to those described above in Example-1. There is a 95% homology between mouse and rat TNF-α, a 90% homology between mouse and rat IL-1β, and an 85% homology between mouse and rat IL-6, and good cross-reactivity is expected.

Adult Sprague-Dawley rats will be anesthetized using 2% isofluorane, shaved, and prepped in the surgical field. Aseptic procedures will be followed, using sterile instruments and sterile preps. Attendees will wear caps, masks, and sterile gloves. Sterile technique will be used in all procedures. Full thickness dermal wounds (1 cm×1 cm) will be created using a scalpel to cut to the fascia over the muscle. The defects will be created bilaterally approximately 5 mm from the spine distal to the rib cage. One side will be treated with the test material and the other side will be used as a control, with treatment side randomized using a random number generator. The animals will then be recovered form anesthesia and allowed normal ambulation and diet for the remainder of the study period. The animal will be anesthetized at 2, 4, and 7 days for photo documentation of the injury site.

Buprenorphine will be given post-operatively for pain (Rat: 0.25 mg/kg, BW, SC q12 h for 5 days). In the following days, the analgesic is given as needed for discomfort evidenced by failure to eat, drink, or resume normal activity. The animals will be monitored daily for infection, inflammation, or delayed healing of the surgical site. If a problem should arise it will be referred to veterinarians and recommendations followed. All animals will receive post-surgical prophylaxis antibiotic therapy (Gentamicin 6 mg/kg, SC, Sid for 3 days).

The animals will be euthanized at one of a 2 day or 14 day identified time point. While under deep anesthesia, the rate will be administered Ketamine 50 mg/kg & Xylazine 10 mg/kg followed by potassium chloride, iv. bolus. The potassium chloride (KCl, ~20% concentration) induces cardiac arrest. Following euthanasia, the operative site will be identified. The site along with an equal amount of adjacent native tissue will be surgically excised and placed in 10% neutral buffered formalin. Following fixation, the specimens will be trimmed, embedded in paraffin, sectioned at 6 microns, and stained with hematoxylin and eosin ("H&E"), Masson's trichrome stain, and anti-myeloperoxidase.

In order to minimize the number of animal experiments that need to be conducted, the TNF-α inhibition experiments will be conducted on full-thickness wounds in healthy rats first. Active inhibition of TNF-α signaling by RGD-HA-anti-TNF-α gels should provide several unambiguous markers, including reduced neutrophil and macrophage invasion, increases in the rate of wound closure, and increases in angiogenesis and collagen production.

Neutrophil invasion into wound sites begins shortly after injury, and if the anti-TNF-α material is active, it should be possible to observe reductions in this marker of inflammation relative to the bilateral control treated with RGD-HA lacking the mAb. Initial experiments will use 2% anti-TNF-α mAb functionalization. Fourteen day time points will be photographed at days 1, 3, 6, and 14 to measure the progress of wound closure and then the wound site and surrounding tissue will be recovered for histological analysis. If no reductions in measures of inflammation are observed relative to the RGD-HA control, experiments using increased concentrations of mAb will be performed with the same time points and measures, starting with 10% then 20% mAb functionalization. If higher concentrations of the anti-TNF-α material do not demonstrate any inhibition of inflammatory responses, IL-1β and IL-6 inhibition will be investigated using the same controls and time points.

Streptozotocin-treated rats will then be treated with the first formulation of the RGD-HA-mAb gels to show biological activity in the healing responses of unhealthy rats. This formulation will be tested in models of diabetes to test whether it is also capable of promoting healing.

The ArrayScan imaging cytometer used in the NF-κB translocation assays described in Example-3 will also be used to perform quantitative histology. Quantitative histology is capable of providing clear statistical assessments on the efficacy of new therapies. Quantitative image analysis can be used to determine degrees of cellular invasion and tissue repair in stained and immunostained tissue sections. Further, scar area, cellular density, dermis thickness, neutrophil density, collagen deposition, and degree of vascularization will be quantified. Because the influences of inhibiting cytokine activities early in the wound healing process may be subtle, it is expected that quantitative histological analyses will provide significant improvements in the preliminary determination of biological activities of RGD-HA-mAb gels in vivo.

Although various embodiments have been described herein, many modifications and variations to those embodiments may be implemented. For example, different types of ligand binding moieties may be employed. Also, where materials are disclosed for certain components (e.g., hyaluronic acid hydrophilic polymer), other materials may be used (e.g., a different GAG). The foregoing description and following claims are intended to cover all such modification and variations.

The invention claimed is:

1. A method for treating wounds, comprising:
   administering to a chronic wound site a composition comprising:
   a hyaluronan matrix; and
   a monoclonal antibody directly conjugated to the hyaluronan matrix, wherein the antibody is selected from the group consisting of an anti-IL-1β, an anti-TNF-α, and combinations thereof.

2. The method of claim 1, wherein the composition further comprises a linear arginine-glycine-aspartic acid (RGD) peptide covalently attached to the hyaluronan matrix.

3. The method of claim 1, wherein the hyaluronan matrix is crosslinked to form a gel-like matrix.

4. The method of claim 1, wherein the composition further comprises a peptide having SEQ ID NO:2 covalently attached to the hyaluronan matrix.

5. The method of claim 1, wherein the composition further comprises a peptide having a sequence selected from the group consisting of SEQ ID NO. 1 and SEQ ID NO. 2 covalently attached to a polymer.

6. The method of claim 1, wherein the composition is used to treat a wound selected from the group consisting of a pressure ulcer, a venous ulcer, and a diabetic ulcer.

7. The method of treatment of claim 1, wherein composition is used to treat a dermal wound.

8. The method of treatment of claim 1, wherein the composition is used to treat a wound in a patient having inflammatory bowel disease.

9. The method of treatment of claim 1, wherein the composition is used to treat a wound in a patient having rheumatoid arthritis.

10. The method of treatment of claim 1, wherein the composition is topically administered directly in a wound.

11. The method of treatment of claim 1, wherein the composition is locally administered by hypodermic injection.

12. The method of treatment of claim 7, wherein the dermal wound is a burn.

* * * * *

SEQUENCE LISTING

```
<160> NUMBER OF SEQ ID NOS: 2

<210> SEQ ID NO 1
<211> LENGTH: 5
<212> TYPE: PRT
<213> ORGANISM: Homo sapiens

<400> SEQUENCE: 1

Gly Arg Gly Asp Ser
1               5

<210> SEQ ID NO 2
<211> LENGTH: 5
<212> TYPE: PRT
<213> ORGANISM: Homo sapiens

<400> SEQUENCE: 2

Tyr Ile Gly Ser Arg
1               5
```